(12) United States Patent
Purdy

(10) Patent No.: US 8,048,140 B2
(45) Date of Patent: Nov. 1, 2011

(54) FENESTRATED INTRALUMINAL STENT SYSTEM

(75) Inventor: James D. Purdy, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 459 days.

(21) Appl. No.: 11/063,085

(22) Filed: Feb. 22, 2005

(65) Prior Publication Data
US 2005/0222669 A1 Oct. 6, 2005

Related U.S. Application Data

(60) Provisional application No. 60/558,168, filed on Mar. 31, 2004.

(51) Int. Cl.
*A61F 2/82* (2006.01)
(52) U.S. Cl. ...................... 623/1.13; 623/1.35
(58) Field of Classification Search .......... 623/1.13, 623/1.35, 1.36, 1.14, 1.16
See application file for complete search history.

(56) References Cited

U.S. PATENT DOCUMENTS

| | | | |
|---|---|---|---|
| 4,562,596 A | 1/1986 | Kornberg | |
| 4,665,918 A | 5/1987 | Garza et al. | |
| 4,950,227 A | 8/1990 | Savin et al. | |
| 4,957,508 A | 9/1990 | Kaneko et al. | 623/12 |
| 5,104,404 A | 4/1992 | Wolff | 623/1 |
| 5,123,917 A | 6/1992 | Lee | 623/1 |
| 5,387,235 A | 2/1995 | Chuter | |
| 5,409,495 A | 4/1995 | Osborn | 606/108 |
| 5,447,497 A | 9/1995 | Sogard et al. | 604/101 |
| 5,522,880 A | 6/1996 | Barone et al. | 623/1 |
| 5,552,880 A | 9/1996 | Shapanus et al. | 365/72 |
| 5,571,173 A | 11/1996 | Parodi | 623/1 |
| 5,578,071 A | 11/1996 | Parodi | 623/1 |
| 5,591,229 A | 1/1997 | Parodi | 623/1 |
| 5,607,444 A | 3/1997 | Lam | 606/194 |
| 5,617,878 A | 4/1997 | Taheri | 128/898 |
| 5,632,762 A | 5/1997 | Myler | 606/194 |
| 5,653,743 A | 8/1997 | Martin | 623/1 |

(Continued)

FOREIGN PATENT DOCUMENTS

EP 0 461 791 A1 6/1991

(Continued)

OTHER PUBLICATIONS

The International Search Report of PCT/US2004/037538 International Filing Date Aug. 11, 2004.

(Continued)

*Primary Examiner* — Ryan Severson
(74) *Attorney, Agent, or Firm* — Brinks Hofer Gilson & Lione

(57) ABSTRACT

An intraluminal prosthesis is provided for strengthening a main lumen and a branch lumen that branches from the main lumen. The intraluminal prosthesis can comprise two tubular grafts. The first tubular graft can have a flexible body with a fenestration. The second tubular graft can have a flexible body that is configured for intraluminal coupling to the fenestration of the first tubular graft. The flexible body of the second tubular graft can have an outer dimension that is about equal to an inner dimension of the fenestration of the first tubular graft. The second tubular graft can also have a terminal stent that curves outwardly from a proximal end of the flexible body of the second tubular graft, whereby the terminal stent acts to couple the second tubular graft to the first tubular graft.

25 Claims, 15 Drawing Sheets

U.S. PATENT DOCUMENTS

| | | | |
|---|---|---|---|
| 5,693,084 A | 12/1997 | Chuter | 623/1 |
| 5,693,087 A | 12/1997 | Parodi | 623/1 |
| 5,720,776 A | 2/1998 | Chuter et al. | |
| 5,755,778 A | 5/1998 | Kleshinski | 623/1 |
| 5,851,228 A * | 12/1998 | Pinheiro | 623/1.13 |
| 5,921,995 A | 7/1999 | Kleshinski | 606/153 |
| 5,957,974 A | 9/1999 | Thompson et al. | 623/1 |
| 5,961,548 A | 10/1999 | Shmulewitz | 623/1 |
| 5,980,531 A | 11/1999 | Goodin et al. | 606/108 |
| 5,984,955 A | 11/1999 | Wisselink | |
| 6,004,347 A * | 12/1999 | McNamara et al. | 623/23.64 |
| 6,010,530 A | 1/2000 | Goicoechea | 623/1 |
| 6,030,414 A | 2/2000 | Taheri | 623/1 |
| 6,036,697 A | 3/2000 | DiCaprio | 606/108 |
| 6,053,941 A | 4/2000 | Lindenberg et al. | 623/1 |
| 6,056,700 A | 5/2000 | Burney et al. | 600/564 |
| 6,059,824 A | 5/2000 | Taheri | 623/1 |
| 6,074,416 A | 6/2000 | Berg et al. | 623/1 |
| 6,077,296 A | 6/2000 | Shokoohi et al. | 623/1 |
| 6,102,940 A | 8/2000 | Robichon et al. | 623/1 |
| 6,152,944 A | 11/2000 | Holman et al. | 606/194 |
| 6,152,956 A | 11/2000 | Pierce | 623/1.13 |
| 6,168,621 B1 | 1/2001 | Vrba | 623/1.2 |
| 6,171,329 B1 | 1/2001 | Shaw et al. | 606/213 |
| 6,176,875 B1 | 1/2001 | Lenker et al. | 623/1.49 |
| 6,187,033 B1 | 2/2001 | Schmitt et al. | 623/1 |
| 6,206,931 B1 | 3/2001 | Cook et al. | |
| 6,210,429 B1 | 4/2001 | Vardi et al. | 623/1.11 |
| 6,217,609 B1 | 4/2001 | Haverkost | 623/1.22 |
| 6,221,090 B1 | 4/2001 | Wilson | 606/194 |
| 6,238,430 B1 | 5/2001 | Klumb et al. | 623/1.13 |
| 6,290,728 B1 | 9/2001 | Phelps et al. | 623/23.7 |
| 6,290,731 B1 | 9/2001 | Solovay et al. | 623/51.16 |
| 6,325,819 B1 | 12/2001 | Pavcnik et al. | 623/1.11 |
| 6,325,826 B1* | 12/2001 | Vardi et al. | 623/1.35 |
| 6,334,869 B1 | 1/2002 | Leonhardt et al. | 623/1.13 |
| 6,344,056 B1 | 2/2002 | Dehdashtian | |
| 6,395,018 B1 | 5/2002 | Castaneda | |
| 6,398,803 B1 | 6/2002 | Layne et al. | |
| 6,409,756 B1 | 6/2002 | Murphy | 623/1.35 |
| 6,409,757 B1 | 6/2002 | Trout, III et al. | 623/1.36 |
| 6,428,565 B1 | 8/2002 | Wisselink | |
| 6,451,050 B1 | 9/2002 | Rudakov et al. | 623/1.15 |
| 6,471,672 B1 | 10/2002 | Brown et al. | 604/101.01 |
| 6,482,227 B1 | 11/2002 | Solovay | 623/1.13 |
| 6,517,574 B1 | 2/2003 | Chuter | 623/1.23 |
| 6,520,988 B1 | 2/2003 | Colombo et al. | |
| 6,524,335 B1 | 2/2003 | Hartley et al. | 623/1.13 |
| 6,527,799 B2 | 3/2003 | Shanley | 623/1.15 |
| 6,572,648 B1 | 6/2003 | Klumb et al. | 623/1.15 |
| 6,582,394 B1 | 6/2003 | Reiss et al. | 604/96.01 |
| 6,585,758 B1 | 7/2003 | Chouinard et al. | 623/1.16 |
| 6,616,675 B1 | 9/2003 | Evard et al. | 606/155 |
| 6,645,242 B1 | 11/2003 | Quinn | 623/1.16 |
| 6,652,567 B1 | 11/2003 | Deaton | |
| 6,663,667 B2 | 12/2003 | Dehdashtian et al. | 623/1.51 |
| 6,669,720 B1 | 12/2003 | Pierce | 623/1.13 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,723,116 B2 | 4/2004 | Taheri | 623/1.11 |
| 6,733,522 B2 | 5/2004 | Schmitt et al. | 623/1.31 |
| 6,733,523 B2 | 5/2004 | Shaolian et al. | 623/1.35 |
| 6,767,358 B2 | 7/2004 | Leonhardt et al. | 623/1.13 |
| 6,773,457 B2 | 8/2004 | Ivancev et al. | 623/1.28 |
| 6,814,752 B1 | 11/2004 | Chuter | 623/1.35 |
| 6,827,735 B2 | 12/2004 | Greenberg | 623/1.25 |
| 6,827,736 B2 | 12/2004 | Perouse | 623/1.36 |
| 6,860,900 B2 | 3/2005 | Clerc et al. | 623/1.35 |
| 6,908,477 B2 | 6/2005 | McGuckin, Jr. et al. | 623/1.11 |
| 7,014,653 B2 | 3/2006 | Ouriel et al. | 623/1.14 |
| 7,108,715 B2 | 9/2006 | Lawrence-Brown et al. | 623/1.21 |
| 7,157,651 B2 | 1/2007 | Rix et al. | 623/1.13 |
| 7,220,275 B2 | 5/2007 | Davidson et al. | 623/1.35 |
| 7,326,237 B2 | 2/2008 | DePalma et al. | 623/1.13 |
| 2001/0027338 A1 | 10/2001 | Greenberg | 623/1.13 |
| 2002/0052648 A1* | 5/2002 | McGuckin et al. | 623/1.35 |
| 2002/0072790 A1 | 6/2002 | McGuckin, Jr. et al. | 623/1.12 |
| 2002/0082684 A1 | 6/2002 | Mishaly | 623/1.36 |
| 2002/0099441 A1 | 7/2002 | Dehdashtian | 623/1.51 |
| 2002/0144696 A1 | 10/2002 | Sharkawy et al. | 128/898 |
| 2002/0156517 A1 | 10/2002 | Perouse | 623/1.11 |
| 2002/0156522 A1 | 10/2002 | Ivancev et al. | 623/1.13 |
| 2002/0193872 A1 | 12/2002 | Trout, III et al. | 623/1.34 |
| 2002/0198585 A1 | 12/2002 | Wisselink | 623/1.11 |
| 2003/0033005 A1 | 2/2003 | Houser et al. | |
| 2003/0074050 A1 | 4/2003 | Kerr | 623/1.13 |
| 2003/0093145 A1 | 5/2003 | Lawrence-Brown et al. | 623/1.21 |
| 2003/0120332 A1* | 6/2003 | Hartley | 623/1.13 |
| 2003/0120333 A1 | 6/2003 | Ouriel et al. | 623/1.14 |
| 2003/0130720 A1 | 7/2003 | DePalma et al. | 623/1.13 |
| 2003/0130724 A1 | 7/2003 | De Palma et al. | 623/1.16 |
| 2003/0199967 A1 | 10/2003 | Hartley et al. | 623/1.13 |
| 2003/0199973 A1 | 10/2003 | Chuter et al. | 623/1.35 |
| 2003/0220682 A1 | 11/2003 | Kujawski | 623/1.13 |
| 2003/0225453 A1 | 12/2003 | Murch | 623/1.21 |
| 2003/0233140 A1 | 12/2003 | Hartley et al. | |
| 2004/0024446 A1 | 2/2004 | Smith | 623/1.22 |
| 2004/0034406 A1* | 2/2004 | Thramann | 623/1.13 |
| 2004/0044396 A1 | 3/2004 | Clerc et al. | 623/1.13 |
| 2004/0054396 A1 | 3/2004 | Hartley et al. | |
| 2004/0059406 A1 | 3/2004 | Cully et al. | 623/1.11 |
| 2004/0073288 A1 | 4/2004 | Kerr | 623/1.13 |
| 2004/0093078 A1 | 5/2004 | Moll et al. | 623/1.35 |
| 2004/0098079 A1 | 5/2004 | Hartley et al. | |
| 2004/0106972 A1 | 6/2004 | Deaton | 623/1.1 |
| 2004/0117004 A1 | 6/2004 | Osborne et al. | 623/1.36 |
| 2004/0133266 A1 | 7/2004 | Clerc et al. | 623/1.22 |
| 2004/0138737 A1 | 7/2004 | Davidsons et al. | 623/1.35 |
| 2004/0167607 A1 | 8/2004 | Frantzen | 623/1.13 |
| 2004/0193254 A1* | 9/2004 | Greenberg et al. | 623/1.35 |
| 2004/0254627 A1 | 12/2004 | Thompson et al. | 623/1.11 |
| 2005/0049678 A1 | 3/2005 | Cocks et al. | 623/1.15 |
| 2005/0149166 A1 | 7/2005 | Schaeffer et al. | 623/1.13 |
| 2005/0171597 A1 | 8/2005 | Boatman et al. | 623/1.22 |
| 2005/0171598 A1 | 8/2005 | Schaeffer | 623/1.35 |
| 2005/0222668 A1 | 10/2005 | Schaeffer et al. | 623/1.13 |
| 2006/0058864 A1 | 3/2006 | Schaeffer et al. | 623/1.11 |
| 2007/0179592 A1 | 8/2007 | Schaeffer | 623/1.35 |

FOREIGN PATENT DOCUMENTS

| | | |
|---|---|---|
| EP | 0 903 118 A2 | 9/1994 |
| EP | 0 646 365 B1 | 1/2004 |
| JP | 404231954 A | 8/1992 |
| JP | 407008512 A | 1/1995 |
| WO | WO 98/22158 A2 | 5/1998 |
| WO | WO 98/53761 A1 | 12/1998 |
| WO | WO 99/29262 A1 | 6/1999 |
| WO | WO 02/067815 A1 | 9/2002 |
| WO | WO 03/020173 A1 | 3/2003 |
| WO | WO 03/034948 A1 | 5/2003 |
| WO | WO 03/053287 A1 | 7/2003 |
| WO | WO 03/065933 | 8/2003 |
| WO | WO 03/082153 | 10/2003 |

OTHER PUBLICATIONS

Office Action for U.S. Appl. No. 10/984,417 dated Nov. 16, 2006, 12 pages.

Amendment After Non-Final Rejection for U.S. Appl. No. 10/984,417 dated Feb. 13, 2007, 11 pages.

Office Action for U.S. Appl. No. 10/984,417 dated May 7, 2007, 14 pages.

Amendment After Final Rejection for U.S. Appl. No. 10/984,417 dated Aug. 10, 2007, 12 pages.

Office Action for U.S. Appl. No. 10/984,417 dated Oct. 10, 2007, 4 pages.

Request for Continued Examination and Response for U.S. Appl. No. 10/984,417 dated Oct. 23, 2007, 11 pages.

Office Action for U.S. Appl. No. 10/984,417 dated Jan. 8, 2008, 6 pages.

Response to Election/Restriction Requirement for U.S. Appl. No. 10/984,417 dated Jan. 31, 2008, 5 pages.

Office Action for U.S. Appl. No. 10/984,417 dated Feb. 26, 2008, 2 pages.
Response to Election/Restriction Requirement for U.S. Appl. No. 10/984,417 dated Mar. 7, 2008, 6 pages.
Office Action for U.S. Appl. No. 10/984,417 dated Jun. 26, 2008, 12 pages.
Amendment After Non-Final Rejection for U.S. Appl. No. 10/984,417 dated Sep. 26, 2008, 12 pages.
Office Action for U.S. Appl. No. 10/984,417 dated Oct. 20, 2008, 2 pages.
Amendment After Non-Final Rejection for U.S. Appl. No. 10/984,417 dated Nov. 3, 2008, 12 pages.
Office Action for U.S. Appl. No. 10/984,417 dated Jul. 29, 2009, 11 pages.
Office Action for U.S. Appl. No. 10/984,417 dated Nov. 20, 2009, 10 pages.
Notice of Appeal for U.S. Appl. No. 10/984,417 dated Feb. 16, 2010, 1 page.
Pre-Appeal Brief Request for Review for U.S. Appl. No. 10/984,417 dated Feb. 16, 2010, 5 pages.
Notice of Panel Decision from Pre-Appeal Brief Review for U.S. Appl. No. 10/984,417 dated Apr. 27, 2010, 2 pages.
Office Action for U.S. Appl. No. 10/984,417 dated Jul. 2, 2010, 10 pages.
Office Action for U.S. Appl. No. 10/984,417 dated Jul. 22, 2010, 13 pages.
Office Action for U.S. Appl. No. 10/984,040 dated May 7, 2007, 8 pages.
Amendment After Non-Final Action for U.S. Appl. No. 10/984,040 dated Sep. 6, 2007, 8 pages.
Office Action for U.S. Appl. No. 10/984,040 dated Nov. 16, 2007, 5 pages.
Amendment After Non-Final Action for U.S. Appl. No. 10/984,040 dated Feb. 18, 2008, 9 pages.
Office Action for U.S. Appl. No. 10/984,040 dated May 1, 2008, 9 pages.
Request for Continued Examination and Amendment for U.S. Appl. No. 10/984,040 dated Sep. 30, 2008, 14 pages.
Office Action for U.S. Appl. No. 10/984,040 dated Oct. 30, 2008, 6 pages.
Applicant Summary of Interview for U.S. Appl. No. 10/984,040 dated Feb. 25, 2009, 2 pages.
Restriction Requirement for U.S. Appl. No. 10/984,040 dated Apr. 28, 2009, 9 pages.
Response to Restriction Requirement for U.S. Appl. No. 10/984,040 dated May 21, 2009, 7 pages.
Restriction Requirement for U.S. Appl. No. 10/984,040 dated Aug. 3, 2009, 6 pages.
Interview Summary for U.S. Appl. No. 10/984,040 dated Oct. 9, 2009, 1 page.
Office Action for U.S. Appl. No. 10/984,040 dated Jan. 29, 2010, 10 pages.
Response to Office Action for U.S. Appl. No. 10/984,040 dated Jul. 21, 2010, 14 pages.
Office Action for U.S. Appl. No. 10/984,416 dated Feb. 20, 2008, 14 pages.
Amendment After Non-Final Rejection for U.S. Appl. No. 10/984,416 dated May 20, 2008, 10 pages.
Office Action for U.S. Appl. No. 10/984,416 dated Aug. 18, 2008, 8 pages.
Request for Continued Examination and Amendment for U.S. Appl. No. 10/984,416 dated Oct. 13, 2008, 13 pages.
Office Action for U.S. Appl. No. 10/984,416 dated Nov. 26, 2008, 10 pages.
Amendment After Non-Final Action for U.S. Appl. No. 10/984,416 dated Mar. 26, 2009, 10 pages.
Office Action for U.S. Appl. No. 10/984,416 dated Jul. 9, 2009, 13 pages.
Interview Summary for U.S. Appl. No. 10/984,416 dated Sep. 15, 2009, 2 pages.
Request for Continued Examination and Amendment for U.S. Appl. No. 10/984,416 dated Oct. 15, 2009, 12 pages.
Office Action for U.S. Appl. No. 10/984,416 dated Feb. 16, 2010, 10 pages.
Amendment and Reply to Office Action for U.S. Appl. No. 10/984,416 dated Jun. 29, 2010, 10 pages.
Office Action for U.S. Appl. No. 10/984,167 dated Nov. 16, 2006, 13 pages.
Amendment After Non-Final Action for U.S. Appl. No. 10/984,167 dated Feb. 15, 2007, 11 pages.
Office Action for U.S. Appl. No. 10/984,167 dated Apr. 27, 2007, 11 pages.
Amendment After Final Rejection for U.S. Appl. No. 10/984,167 dated Aug. 27, 2007, 9 pages.
Advisory Action for U.S. Appl. No. 10/984,167 dated Sep. 18, 2007, 3 pages.
Request for Continued Examination and Amendment for U.S. Appl. No. 10/984,167 dated Sep. 27, 2007, 10 pages.
Office Action for U.S. Appl. No. 10/984,167 dated Oct. 30, 2007, 10 pages.
Amendment After Non-Final Action for U.S. Appl. No. 10/984,167 dated Jan. 28, 2008, 9 pages.
Office Action for U.S. Appl. No. 10/984,167 dated Apr. 22, 2008, 11 pages.
Request for Continued Examination and Amendment for U.S. Appl. No. 10/984,167 dated Sep. 22, 2008, 11 pages.
Office Action for U.S. Appl. No. 10/984,167 dated Nov. 28, 2008, 10 pages.
Amendment after Non-Final Action for U.S. Appl. No. 10/984,167 dated Mar. 30, 2009, 13 pages.
Office Action for U.S. Appl. No. 10/984,167 dated Jun. 1, 2009, 11 pages.
Amendment After Final Action for U.S. Appl. No. 10/984,167 dated Aug. 3, 2009, 8 pages.
Advisory Action for U.S. Appl. No. 10/984,167 dated Aug. 13, 2009, 3 pages.
Notice of Appeal for U.S. Appl. No. 10/984,167 dated Sep. 1, 2009, 1 page.
Request for Pre-Appeal Review for U.S. Appl. No. 10/984,167 dated Sep. 1, 2009, 6 pages.
Pre-Appeal Panel Decision for U.S. Appl. No. 10/984,167 dated Nov. 24, 2009, 2 pgs.
Office Action for U.S. Appl. No. 10/984,167 dated Mar. 29, 2010, 10 pages.
Office Action for U.S. Appl. No. 10/984,131 dated Nov. 16, 2006, 12 pages.
Amendment After Non-Final Rejection for U.S. Appl. No. 10/984,131 dated Mar. 16, 2007, 10 pages.
Office Action for U.S. Appl. No. 10/984,131 dated Jun. 22, 2007, 12 pages.
Amendment After Final Rejection for U.S. Appl. No. 10/984,131 dated Aug. 22, 2007, 11 pages.
Advisory Action for U.S. Appl. No. 10/984,131 dated Sep. 18, 2007, 3 pages.
Request for Continued Examination and Amendment for U.S. Appl. No. 10/984,131 dated Sep. 28, 2007, 11 pages.
Office Action for U.S. Appl. No. 10/984,131 dated Dec. 12, 2007, 13 pages.
Amendment After Non-Final Action for U.S. Appl. No. 10/984,131 dated Apr. 14, 2008, 10 pages.
Office Action for U.S. Appl. No. 10/984,131 dated Aug. 14, 2008, 14 pages.
Request for Continued Examination and Amendment for U.S. Appl. No. 10/984,131 dated Oct. 13, 2008, 14 pages.
Office Action for U.S. Appl. No. 10/984,131 dated Jan. 5, 2009, 10 pages.
Amendment After Non-Final Action for U.S. Appl. No. 10/984,131 dated May 5, 2009, 10 pages.
Office Action for U.S. Appl. No. 10/984,131 dated Jul. 24, 2009, 12 pages.
Amendment After Final Rejection for U.S. Appl. No. 10/984,131 dated Sep. 24, 2009, 10 pages.
Advisory Action for U.S. Appl. No. 10/984,131 dated Oct. 5, 2009, 3 pages.

Notice of Appeal for U.S. Appl. No. 10/984,131 dated Oct. 26, 2009, 1 page.
Request for Pre-Appeal Review for U.S. Appl. No. 10/984,131 dated Oct. 26, 2009, 6 pages.
Pre-Appeal Panel Decision for U.S. Appl. No. 10/984,131 dated Dec. 23, 2009, 2 pages.
Office Action for U.S. Appl. No. 10/984,131 dated Mar. 26, 2010, 11 pages.
Office Action for U.S. Appl. No. 10/984,520 dated Nov. 27, 2006, 16 pages.
Amendment After Non-Final Rejection for U.S. Appl. No. 10/984,520 dated Feb. 27, 2007, 16 pages.
Office Action for U.S. Appl. No. 10/984,520 dated May 15, 2007, 10 pages.
Amendment After Final Rejection for U.S. Appl. No. 10/984,520 dated Aug. 15, 2007, 8 pages.
Advisory Action for U.S. Appl. No. 10/984,520 dated Sep. 6, 2007, 3 pages.
Request for Continued Examination and Amendment for U.S. Appl. No. 10/984,520 dated Oct. 15, 2007, 9 pages.
Office Action for U.S. Appl. No. 10/984,520 dated Dec. 28, 2007, 8 pages.
Amendment After Non-Final Rejection for U.S. Appl. No. 10/984,520 dated Mar. 28, 2008, 8 pages.
Office Action for U.S. Appl. No. 10/984,520 dated Jun. 23, 2008, 9 pages.
Request for Continued Examination and Amendment for U.S. Appl. No. 10/984,520 dated Sep. 22, 2008, 14 pages.
Office Action for U.S. Appl. No. 10/984,520 dated Dec. 9, 2008, 8 pages.
Amendment After Non-Final Rejection for U.S. Appl. No. 10/984,520 dated May 11, 2009, 9 pages.
Office Action for U.S. Appl. No. 10/984,520 dated Aug. 17, 2009, 10 pages.
Notice of Appeal for U.S. Appl. No. 10/984,520 dated Feb. 16, 2010, 1 page.
Pre-Appeal Brief Request for Review for U.S. Appl. No. 10/984,520 dated Feb. 16, 2010, 5 pages.
Notice of Panel Decision from Pre-Appeal Brief Review for U.S. Appl. No. 10/984,520 dated Mar. 11, 2010, 2 pages.
Appeal Brief for U.S. Appl. No. 10/984,520 dated May 24, 2010, 25 pages.
Examiner's Answer for U.S. Appl. No. 10/984,520 dated Jul. 21, 2010, 9 pages.

* cited by examiner

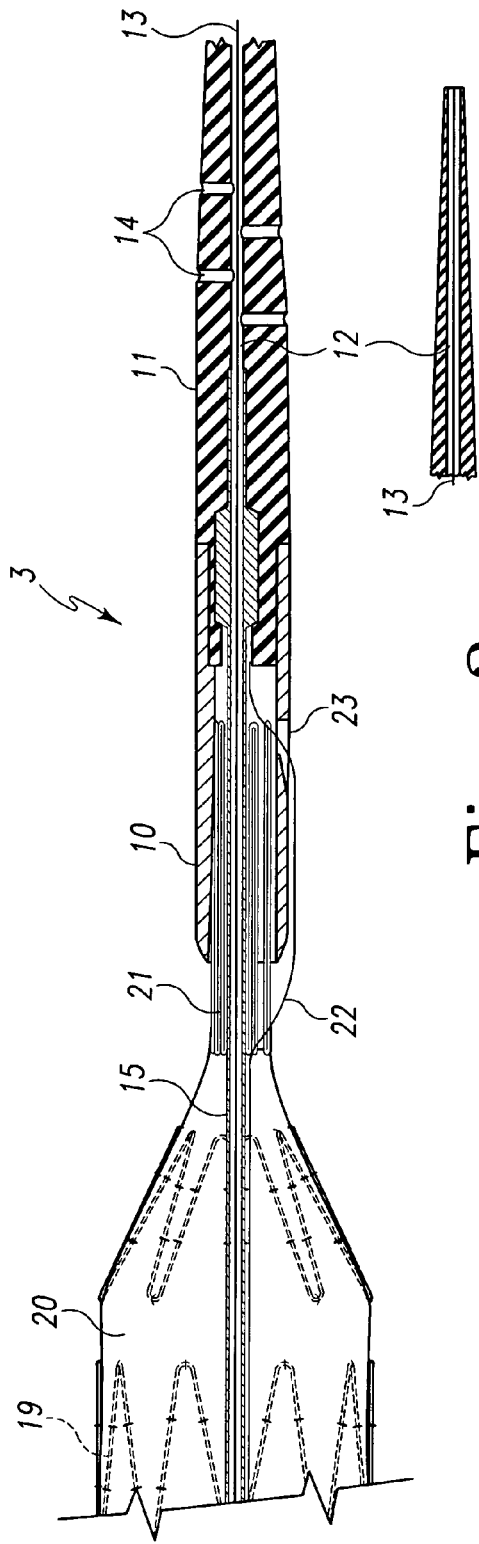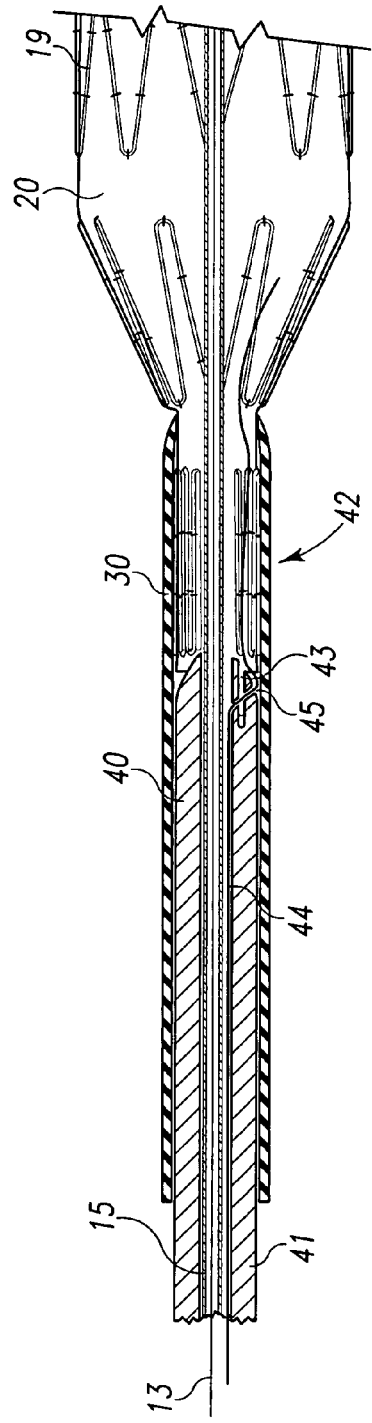
Fig. 2
Fig. 3

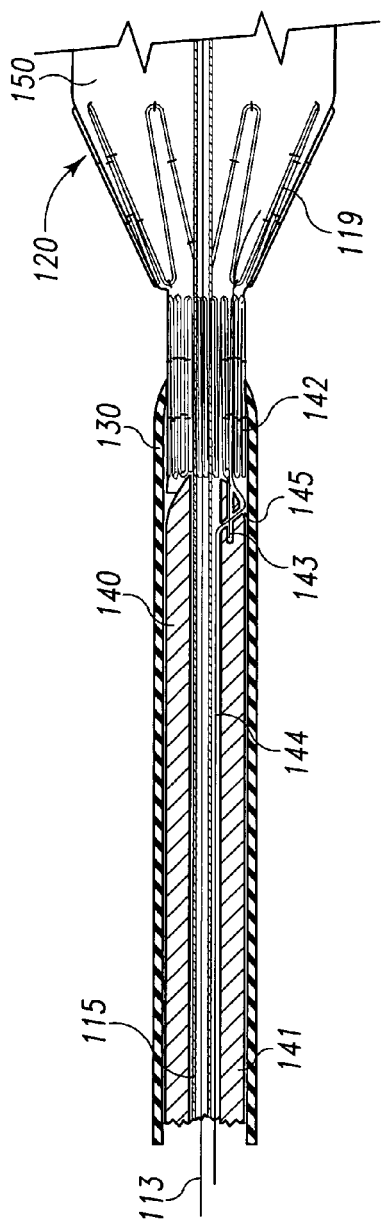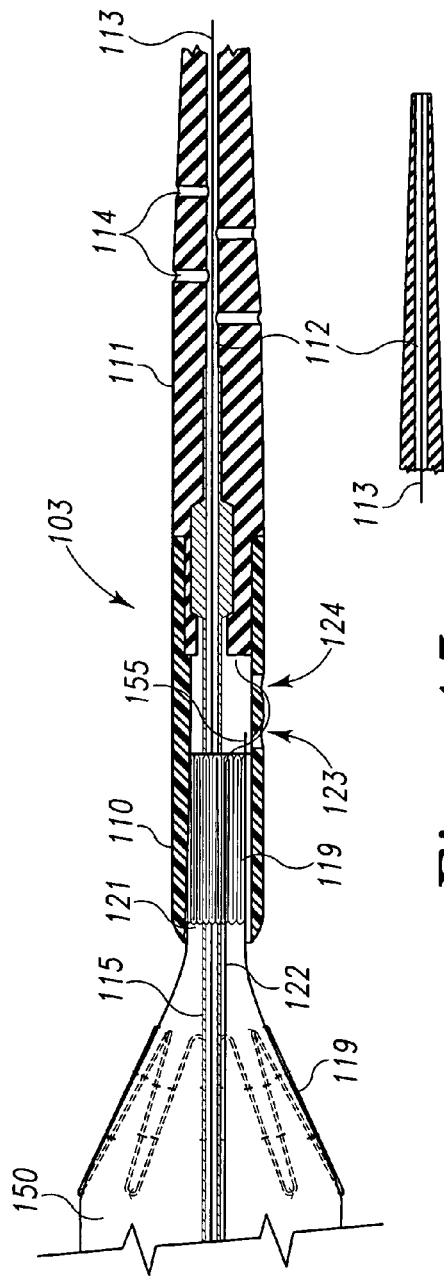

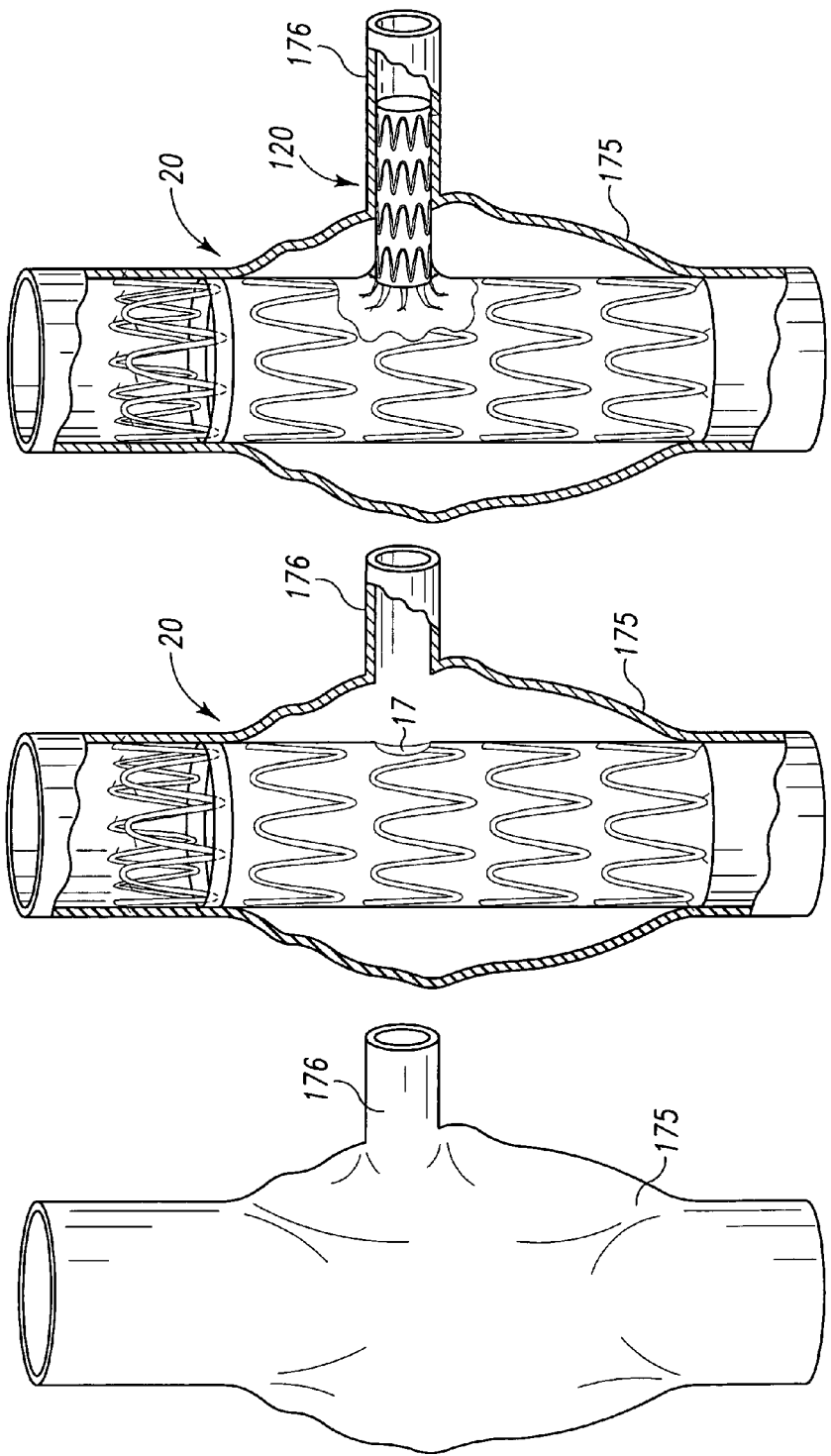

FENESTRATED INTRALUMINAL STENT SYSTEM

CROSS-REFERENCE TO RELATED APPLICATIONS

This application is related to, and claims all benefits of, U.S. Provisional Application No. 60/558,168 filed Mar. 31, 2004.

BACKGROUND OF THE INVENTION

1. Technical Field

This invention relates to a medical device and, in particular, a prosthesis for implantation within the human or animal body for the repair of damaged vessels such as blood vessels, and a method for implanting the same.

2. Related Art

Throughout this specification, when discussing the aorta or other blood vessels, the terms distal and distally with respect to a prosthesis are intended to refer to the end of the prosthesis furthest away in the direction of blood flow from the heart. Similarly, the terms proximal and proximally are intended to mean the end of the prosthesis which when implanted would be nearest to the heart.

The functional vessels of humans, such as blood vessels and ducts, occasionally weaken or even rupture. For example, the aortic wall can weaken, resulting in an aneurysm. Upon further exposure to haemodynamic forces, such an aneurysm can rupture. A common surgical intervention for weakened, aneurismal or ruptured vessels is the use of a prosthesis to provide some or all of the functionality of the original, healthy vessel and/or preserve any remaining vascular integrity by replacing a length of the existing vessel wall that spans the site of vessel failure.

The deployment of intraluminal prostheses into the lumen of a patient from a remote location by the use of a deployment device or introducer has been disclosed in a number of earlier patents and patent applications. U.S. Pat. No. 4,562,596, entitled "Aortic Graft, Device and Method for Performing an Intraluminal Abdominal Aortic Aneurysm Repair" which is herein incorporated by reference, proposes the retention of a self expanding graft within a sleeve until it is to be deployed, at which time the sleeve is withdrawn and the graft is allowed to expand. U.S. Pat. No. 4,665,918, entitled "Prosthesis System and Method" which is herein incorporated by reference, proposes a system and method for the deployment of a prosthesis in a blood vessel. The prosthesis is positioned between a delivery catheter and an outer sheath and expands outwardly upon removal of the sheath.

U.S. Pat. No. 4,950,227, entitled "Stent Delivery System" which is herein incorporated by reference, proposes the delivery of a stent by mounting the stent to the outside of an inflatable catheter and retaining the ends of an unexpanded stent by fitting a sleeve over either end of the stent. Expansion of the stent is caused by inflation of the catheter between the sleeves so that the ends of the stent are withdrawn from the respective sleeves and the stent released and expanded into position.

U.S. Pat. No. 5,387,235 entitled "Expandable Transluminal Prosthesis for Repair of Aneurysm", discloses apparatus and methods of retaining grafts onto deployment devices. These features and other features disclosed in U.S. Pat. No. 5,387,235 could be used with the present invention and the disclosure of U.S. Pat. No. 5,387,235 is herein incorporated by reference.

U.S. Pat. No. 5,720,776 entitled "Barb and Expandable Transluminal Graft Prosthesis for Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herein incorporated by reference.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herein incorporated by reference.

PCT Patent Publication Number No. WO99/29262 entitled "Endoluminal Aortic Stents" discloses a fenestrated prosthesis for placement where there are intersecting arteries. This feature and other features disclosed in PCT Patent Publication Number No. WO99/29262 could be used with the present invention and the disclosure of PCT Patent Publication Number No. WO99/29262 is herein incorporated by reference.

PCT Patent Publication Number No. WO03/034948 entitled "Prostheses for Curved Lumens" discloses prostheses with arrangements for bending the prosthesis for placement into curved lumens. This feature and other features disclosed in PCT Patent Publication Number No. WO03/034948 could be used with the present invention and the disclosure of PCT Patent Publication Number No. WO03/034948 is herein incorporated by reference.

U.S. Patent Application Publication No. 2003/0233140 entitled "Trigger Wire System" discloses release wire systems for the release of stent grafts retained on introducer devices. This feature and other features disclosed in U.S. Patent Application Publication No. 2003/0233140 could be used with the present invention and the disclosure of U.S. Patent Application Publication No. 2003/0233140 is herein incorporated by reference.

U.S. Patent Application Publication No. 2004/0098079 entitled "Thoracic Deployment Device" discloses introducer devices adapted for deployment of stent grafts particularly in the thoracic arch. This feature and other features disclosed in U.S. Patent Application Publication No. 2004/0098079 could be used with the present invention and the disclosure of U.S. Patent Application Publication No. 2004/0098079 is herein incorporated by reference.

U.S. Patent Application Publication No. 2004/0054396 entitled "Stent-Graft Fastening" discloses arrangements for fastening stents onto grafts particularly for exposed stents. This feature and other features disclosed in U.S. Patent Application Publication No. 2004/0054396 could be used with the present invention and the disclosure of United States Patent Application Publication No. 2004/0054396 is herein incorporated by reference.

PCT Patent Publication Number No. WO03/053287 entitled "Stent Graft with Improved Graft Adhesion" discloses arrangements on stent grafts for enhancing the adhesion of such stent grafts into walls of vessels in which they are deployed. This feature and other features disclosed in PCT Patent Publication Number No. WO03/053287 could be used with the present invention and the disclosure of PCT Patent Publication Number No. WO03/053287 is herein incorporated by reference.

PCT Patent Publication Number No. WO98/53761 entitled "A Prosthesis and a Method and Means of Deploying a Prosthesis", which is herein incorporated by reference, discloses various embodiments of an introducer for positioning an expandable endovascular prosthesis in a lumen of a patient.

One issue that arises with the use of an intraluminal prosthesis is where the damage in a vessel is at or near a branching vessel. For example, an abdominal aortic aneurysm can exist near the renal arteries, and a thoracic aortic aneurysm can exist near the left subclavian, common carotid, and/or innominate arteries. It would be desirable to prevent the prostheses from obstructing such a branch vessel. It may also be desirable to include a fenestration in a wall of an intraluminal prosthesis to allow fluid communication between the interior cavity of the prosthesis and a branch vessel adjacent to the prostheses. It may be further desirable to maintain an alignment between such a fenestration and an opening to a branch vessel.

SUMMARY

An intraluminal prosthesis is provided for strengthening a main lumen and a branch lumen in direct fluid communication with the main lumen. The prosthesis comprises a first tubular graft having a first flexible body, which includes a wall with a fenestration having a linear dimension. The prosthesis also comprises a second tubular graft having a second flexible body. The second tubular graft also includes a self-expanding stent with a terminal loop coupled that is coupled to a longitudinal end of the second flexible body. The self-expanding stent, when in an expanded state, has curvature such that the terminal loop is substantially in the same plane as the longitudinal end of the second flexible body. The second tubular graft is configured for endoluminal coupling with the first tubular graft.

An intraluminal prosthesis is provided for strengthening a branch lumen. The intraluminal prosthesis can comprise a flexible body made from a graft material and having a tubular interior passage. The prosthesis can also comprise a plurality of self expanding stents coupled along the length of the flexible body. A terminal stent can be coupled to and extend substantially radially outwardly from the proximal end of the flexible body.

A method of assembling a prosthesis intraluminally is also provided. The method can include providing a first tubular graft that has an inner passage, an outer surface, and a fenestration through the outer surface to the inner passage. The method can further include providing a second tubular graft having an inner passage, an outer surface, and a proximal end. The method can also include inserting the proximal end of the second tubular graft into the fenestration of the first tubular graft, and coupling the second tubular graft to the first tubular graft so that the inner passage of the second tubular graft is in fluid communication with the inner passage of the first tubular graft.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 2 is a sectional view of a portion of the introducer around the proximal end of the prosthesis.

FIG. 3 is a sectional view of a portion of the introducer around the distal end of the prosthesis.

FIG. 14 is a sectional view of a portion of the introducer of FIG. 13 around the proximal end of the branch prosthesis.

FIG. 15 is a sectional view of a portion of the introducer of FIG. 13 around the distal end of the branch prosthesis.

FIG. 17 is an elevation view of a main lumen and a branch lumen in fluid communication with the main lumen.

FIG. 18 is a sectional view of the main lumen and the branch lumen of FIG. 17 after the prosthesis of FIGS. 1A and 1B has been implanted.

FIG. 19 is a sectional view of the main lumen and the branch lumen of FIG. 17 after the branch prosthesis of FIG. 13 has been implanted in the prosthesis of FIG. 1A through the fenestration shown in FIG. 1B.

DETAILED DESCRIPTION OF THE PREFERRED EMBODIMENTS

Figure 1:
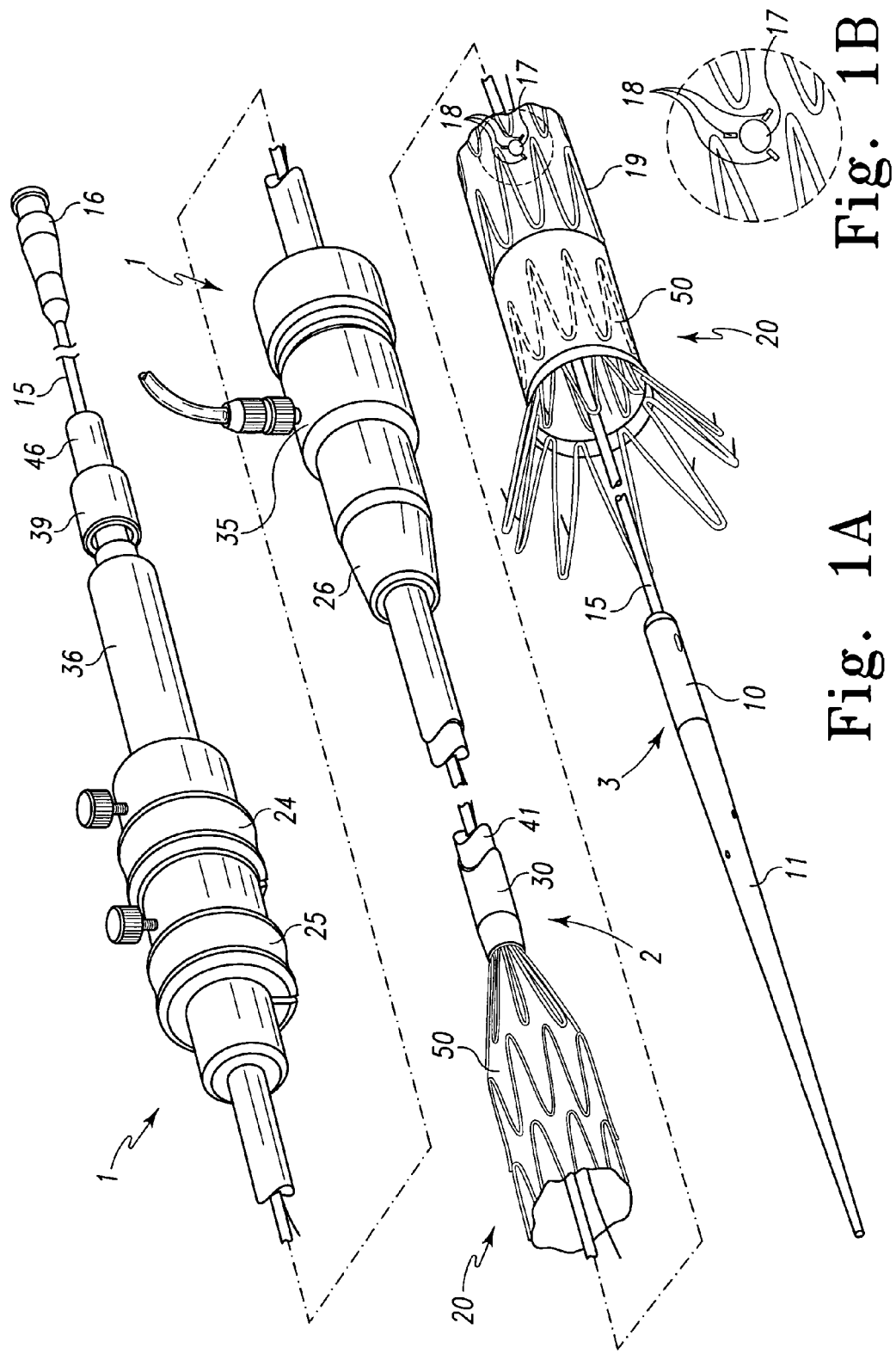
FIG. 1A is an exploded perspective view of an introducer a prosthesis partially deployed.
FIG. 1B is detail perspective view of a portion of the prosthesis shown in FIG. 1A.

FIG. 1A shows an endoluminal prosthesis 20, and an endovascular deployment system, also known as an introducer, for deploying the prosthesis 20 in a lumen of a patient during a medical procedure. The term "prosthesis" means any replacement for a body part or function of that body part. It can also mean a device that enhances or adds functionality to a physiological system. The terms "intraluminal" and "endoluminal" describes objects that are found or can be placed inside a lumen in the human or animal body. A lumen can be an existing lumen or a lumen created by surgical intervention. This includes lumens such as blood vessels, parts of the gastrointestinal tract, ducts such as bile ducts, parts of the respiratory system, etc. "Endoluminal prosthesis" or "Intraluminal prosthesis" thus describes a prosthesis that can be placed inside one of these lumens.

The introducer shown in FIG. 1A includes an external manipulation section 1, a distal positioning mechanism attachment region 2 and a proximal positioning mechanism attachment region 3. During the medical procedure to deploy the prosthesis 20, the distal and proximal attachment regions 2 and 3 will travel through the lumen to a desired deployment site. The external manipulation section 1, which is acted upon by a user to manipulate the introducer, remains outside of the patient throughout the procedure.

The prosthesis 20 comprises a tubular graft material 50, with self expanding stents 19 attached thereto. The term "graft" means the generally cannular or tubular member which acts as an artificial vessel. A graft by itself or with the addition of other elements can be an endoluminal prosthesis. The term "stent" means any device or structure that adds rigidity, expansion force or support to a prosthesis.

The tubular graft material 50 is preferably non-porous so that it does not leak or sweat under physiologic forces. The graft material is preferably made of woven DACRON® polyester (VASCUTEK® Ltd., Renfrewshire, Scotland, UK). The tubular graft can be made of any other at least substantially biocompatible material including such materials as other polyester fabrics, polytetrafluoroethylene (PTFE), expanded PTFE, and other synthetic materials known to those of skill in the art. Naturally occurring biomaterials, such as collagen, are also highly desirable, particularly a derived collagen material known as extracellular matrix (ECM), such as small intestinal submucosa (SIS).

Other examples of ECMs are pericardium, stomach submucosa, liver basement membrane, urinary bladder submucosa, tissue mucosa, and dura mater. SIS is particularly useful, and can be made in the fashion described in U.S. Pat. No. 4,902,508 to Badylak et al.; U.S. Pat. No. 5,733,337 to Carr; 17 Nature Biotechnology 1083 (November 1999); and WIPO Publication WO 98/22158 of May 28, 1998, to Cook et al., which is the published application of PCT/US97/14855. All of these patents and publications are incorporated herein by reference.

Irrespective of the origin of the graft material (synthetic versus naturally occurring), the graft material can be made thicker by making multi-laminate constructs, for example SIS constructs as described in U.S. Pat. No. 5,968,096, U.S. Pat. No. 5,955,110, U.S. Pat. No. 5,885,619, and U.S. Pat. No. 5,711,969. All of these patents are incorporated herein by reference. In addition to xenogenic biomaterials, such as SIS, autologous tissue can be harvested as well, for use in forming the graft material. Additionally elastin or elastin-like polypeptides (ELPs) and the like offer potential as a material to fabricate the graft material.

The self expanding stents 19 cause the prosthesis 20 to expand following its disengagement from the introducer. The prosthesis 20 also includes a self expanding zigzag stent 21 that extends from its proximal end. When it is disengaged, the self expanding zigzag stent 21 anchors the proximal end of the prosthesis 20 to the lumen.

One or more fenestrations 17 can be provided in the tubular graft material 50. Radiographic markers 18 can be attached to the tubular graft material 50 adjacent to the fenestration 17 as shown in FIG. 1B in order to aid in the alignment of the fenestration 17 with a branch vessel. For example, the radiographic markers 18 can be small rings of metal, such as stainless steel, sewn to the tubular graft material 50 with suture, not shown.

FIG. 2 shows the proximal attachment region 3 in greater detail. The proximal attachment region 3 includes a cylindrical sleeve 10. The cylindrical sleeve 10 has a long tapered flexible extension 11 extending from its proximal end. The flexible extension 11 has an internal longitudinal aperture 12. The longitudinal aperture 12 facilitates advancement of the tapered flexible extension 11 along an insertion wire 13. The aperture 12 also provides a channel for the introduction of medical reagents, which will flow through openings 14. For example, it may be desirable to supply a contrast agent to allow angiography to be performed during placement and deployment phases of the medical procedure.

A thin walled tube 15, which can be made of metal, is fastened to the extension 11. The thin walled tube 15 is sufficiently flexible so that the introducer can be advanced along a relatively tortuous vessel, such as a femoral artery. The thin walled tube 15 also facilitates manipulation longitudinally and rotationally of the proximal attachment region 3. The thin walled tube 15 extends through the introducer to the manipulation section 1, terminating at a connection means 16, as shown in FIG. 6.

Figure 6:
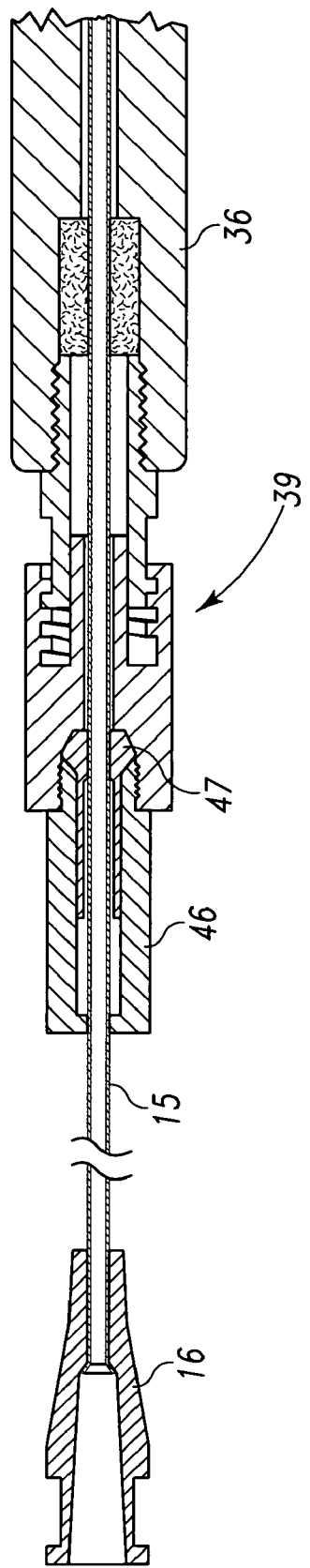
FIG. 6 is a sectional view of a portion of the introducer around the pin vise clamp and the medical reagent introduction tube.

Regarding the introduction of reagents, FIG. 6 also shows that the connection means 16 is adapted to accept a syringe to facilitate the introduction of reagents into the tube 15. The tube 15 is in fluid communication with the aperture 12 of the flexible extension 11. Therefore, reagents introduced into connection means 16 flow through the aperture 12 and emanate from the apertures 14.

Figure 5:
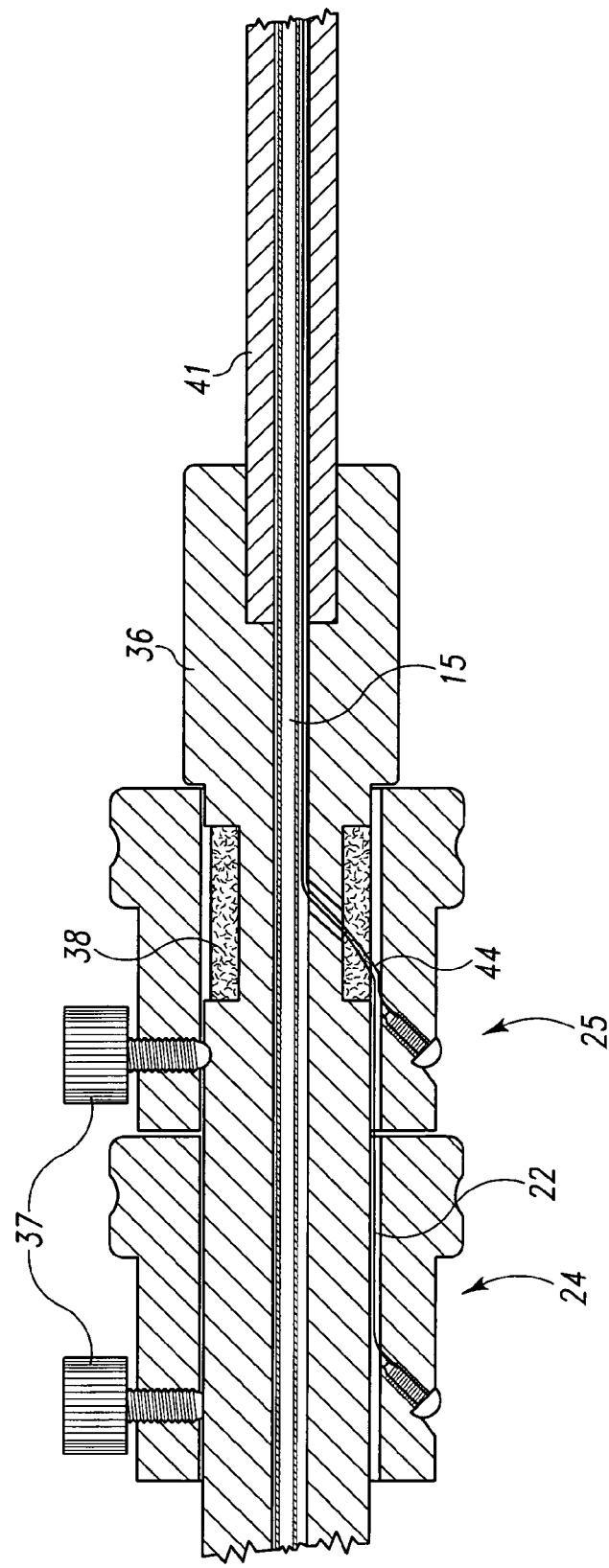
FIG. 5 is a sectional view of a portion of the introducer around the trigger wire release mechanisms.

As shown in FIG. 3, a tube 41, which can be made of plastic, is coaxial with and radially outside the thin walled tube 15. The tube 41 is "thick walled", that is to say the thickness of its wall is several times that of the thin walled tube 15. A sheath 30 is coaxial with and radially outside the thick walled tube 41. The thick walled tube 41 and the sheath 30 extend distally to the manipulation region 1, as shown in FIG. 5.

FIGS. 2 and 3 illustrate distal and proximal retention and release mechanisms of the introducer, respectively. During the placement phase of the medical procedure, the prosthesis 20 is retained in a compressed condition by the sheath 30. The sheath 30 extends distally to a gripping and haemostatic sealing means 35 of the external manipulation section 1, shown in FIG. 4.

During assembly of the introducer, the sheath 30 is advanced over the cylindrical sleeve 10 of the proximal attachment region 3 while the prosthesis 20 is held in a compressed state by an external force. A distal attachment retention section 40 is formed in the thick walled tube 41 to retain the distal end of the prosthesis 20. Alternatively, the distal attachment section 40 can be a separate piece coupled to the thick walled tube 41.

The self-expanding stent 21 is released by retracting the sheath 30, removing the trigger wire 22, and then sliding the proximal attachment region 3, including the retention device 10, proximally away from the stent 21. Once the retention device 10 has cleared the self-expanding stent 21, the stent 21 will expand. The trigger wire 22 and the proximal wire release mechanism 24 form a control member to selectively release the retention device 10 from the prosthesis 20 by holding the self-expanding stent 21 in the retention device 10 until the prosthesis 20 is positioned at a desired site in the lumen.

The distal end 42 of the prosthesis 20 is retained by the distal attachment section 40 of the thick walled tube 41. The distal end 42 of the prosthesis 20 has a loop 43 through which a distal trigger wire 44 extends. The distal trigger wire 44 extends through an aperture 45 in the distal attachment section 40 into the annular region between the thin walled tube 15 and the thick walled tube 41.

As shown in FIG. 5, the distal trigger wire 44 extends through the annular space between the thick walled tube 41 and the thin walled tube 15 to the manipulation region 1. The distal trigger wire 44 exits the annular space at a distal wire release mechanism 25. The distal trigger wire 44 and the distal wire release mechanism 25 form a control member to selectively disengage the distal retention section 40 from the prosthesis 20 when it is positioned at a desired site in the lumen.

Figure 4:
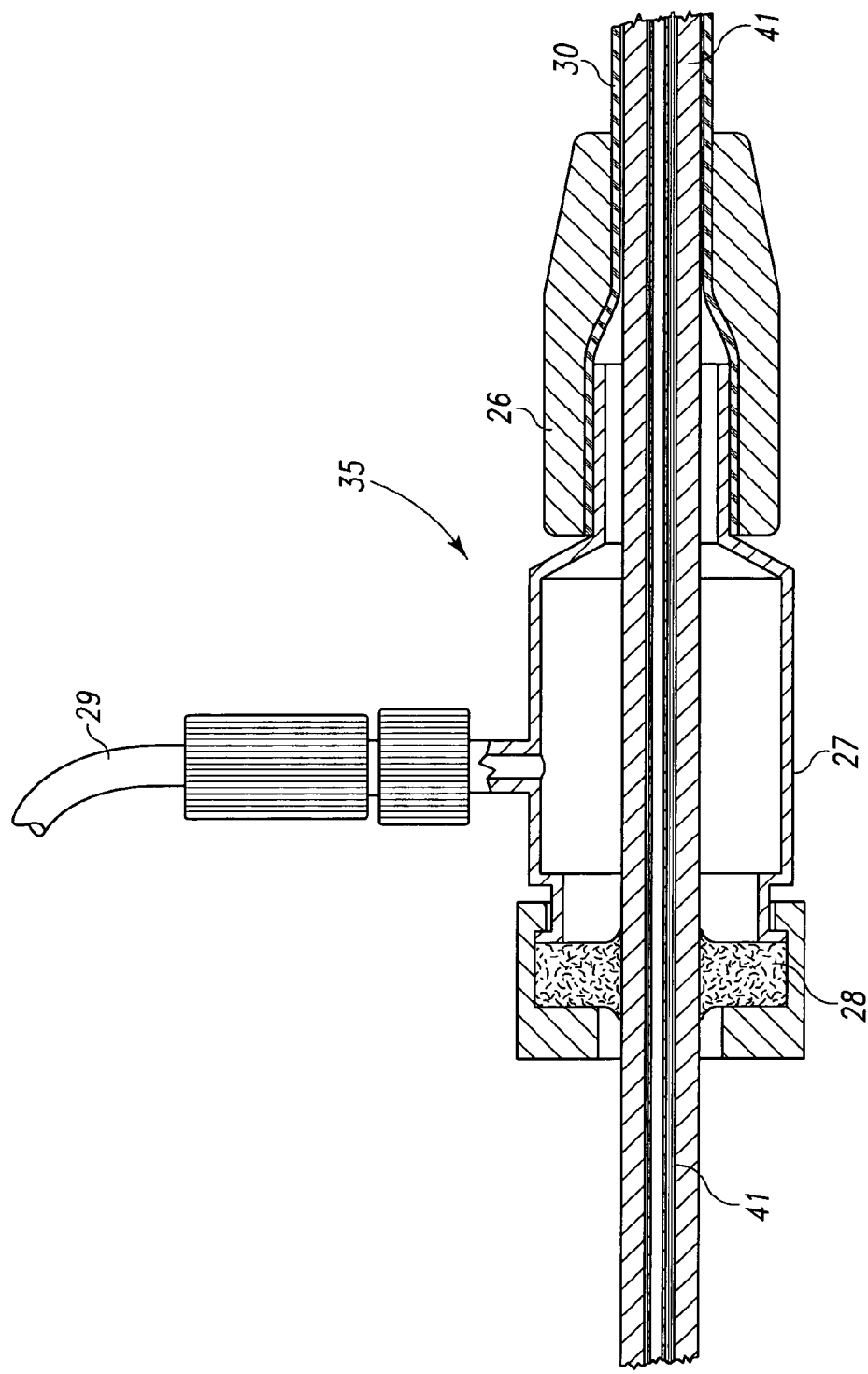
FIG. 4 is a sectional view of a portion of the introducer around the haemostatic seal.

FIG. 4 shows the haemostatic sealing means 35 of the external manipulation section 1 in greater detail. The haemostatic sealing means 35 includes a haemostatic seal 27 and a side tube 29. The haemostatic seal 27 includes a clamping collar 26 that clamps the sheath 30 to the haemostatic seal 27. The haemostatic seal 27 also includes a silicone seal ring 28. The silicone seal ring 28 forms a haemostatic seal around the thick walled tube 41. The side tube 29 facilitates the introduction of medical reagents between the thick walled tube 41 and the sheath 30.

FIG. 5 shows a proximal portion of the external manipulation section 1. The release wire actuation section has a body 36 that is mounted onto the thick walled tube 41. The thin walled tube 15 passes through the body 36. The distal wire release mechanism 25 is mounted for slidable movement on the body 36. Similarly, the proximal wire release mechanism 24 is mounted for slidable movement on the body 36. A pair of clamping screws 37 prevent inadvertent early release of the prosthesis 20.

The positioning of the proximal and distal wire release mechanisms 24 and 25 is such that the proximal wire release mechanism 24 must be moved before the distal wire release mechanism 25 can be moved. Therefore, the distal end 42 of the prosthesis 20 cannot be released until the self-expanding zigzag stent 21 has been released and anchored to the lumen. A haemostatic seal 38 is provided so the release wires 22 and 44 can extend out through the body 36 to the release mechanisms 24 and 25 without unnecessary blood loss during the medical procedure.

FIG. 6 shows a distal portion of the external manipulation section 1. A pin vise 39 is mounted onto the distal end of the body 36. The pin vise 39 has a screw cap 46. When screwed in, the vise jaws 47 clamp against (engage) the thin walled tube 15. When the vise jaws 47 are engaged, the thin walled tube 15 can only move with the body 36, and hence the thin walled tube 15 can only move with the thick walled tube 41. With the screw cap 46 tightened, the entire assembly, except for the external sleeve 30, can be moved as one.

The prosthesis 20 can be deployed in any method known in the art, preferably the method described in WO98/53761 in which the devise is inserted by an introducer via a surgical cut-down into a femoral artery, and then advanced into the desired position over a stiff wire guide 13, shown in FIGS. 2 and 3, using endoluminal interventional techniques. For example, FIGS. 7 through 12 show various stages of the deployment of the prosthesis 20 during an illustrative medical procedure. A guide wire 13 is introduced into the femoral artery and advanced until its tip is beyond the region into which the prosthesis 20 is to be deployed.

Figure 7:
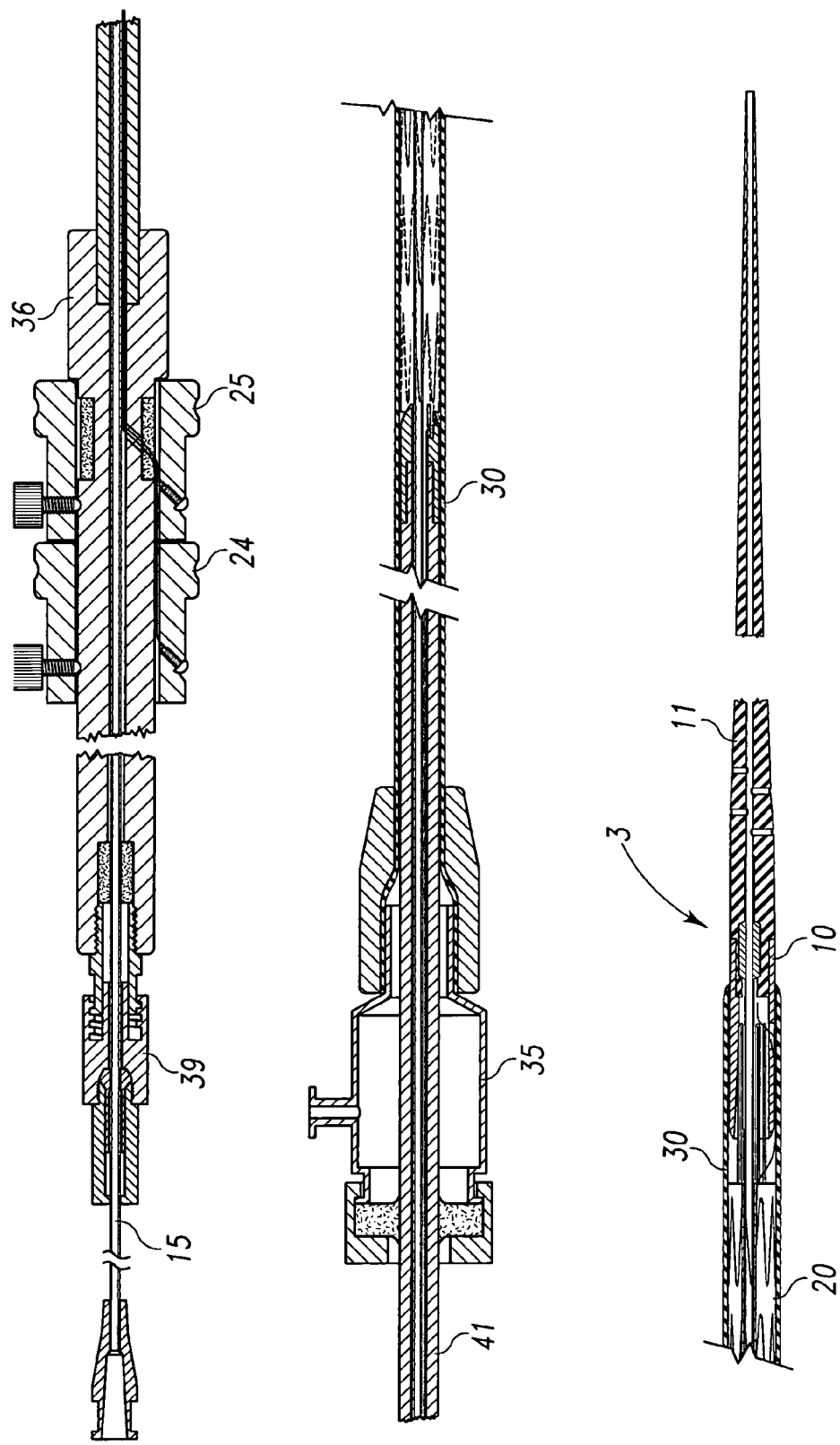
FIG. 7 is an exploded sectional view of the introducer of FIG. 1A fully loaded and ready for introduction into a patient.

In FIG. 7, the introducer assembly is shown fully assembled ready for introduction into a patient. The prosthesis 20 is retained at each of its ends by the proximal and distal retaining assemblies respectively, and compressed by the external sleeve 30. If it is an aortic aneurism which is to be grafted, the introducer assembly can be inserted through a femoral artery over the guide wire 13 in the form as shown in FIG. 7, and positioned by well known radiographic techniques not discussed here. The fenestration 17 of the prosthesis 20 can be aligned with a branch vessel, such as a renal artery, during this positioning.

Figure 8:
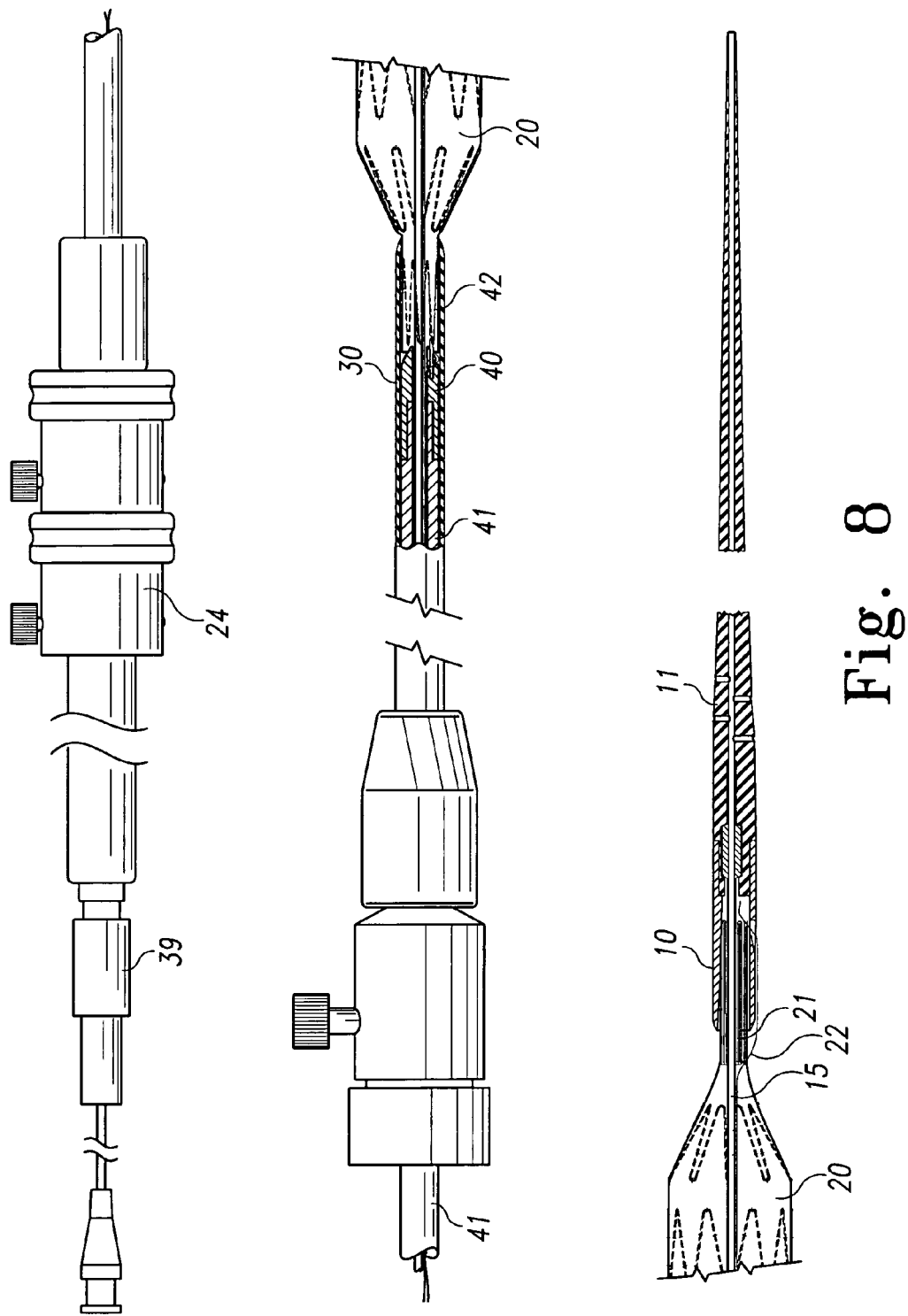
FIG. 8 is an exploded view partially in section of the introducer of FIG. 7 in the next stage of deployment of the prosthesis.

In FIG. 8, the introducer assembly is in a desired position for deployment of the prosthesis 20. The external sheath 30 is withdrawn to just proximal of the distal attachment section 40. This action releases the middle portion of the prosthesis 20 so that it can expand radially. The proximal self-expanding stent 21, however, is still retained within the retention device 10. Also, the distal end 42 of the prosthesis 20 is still retained within the external sheath 30.

By release of the pin vise 39 to allow small movements of the thin walled tubing 15 with respect to the thick walled tubing 41, the prosthesis 20 can be lengthened or shortened or rotated or compressed for accurate placement in the desired location within the lumen. X-ray opaque markers, not shown, can be placed along the prosthesis 20 to assist with placement of the prosthesis.

Figure 9:
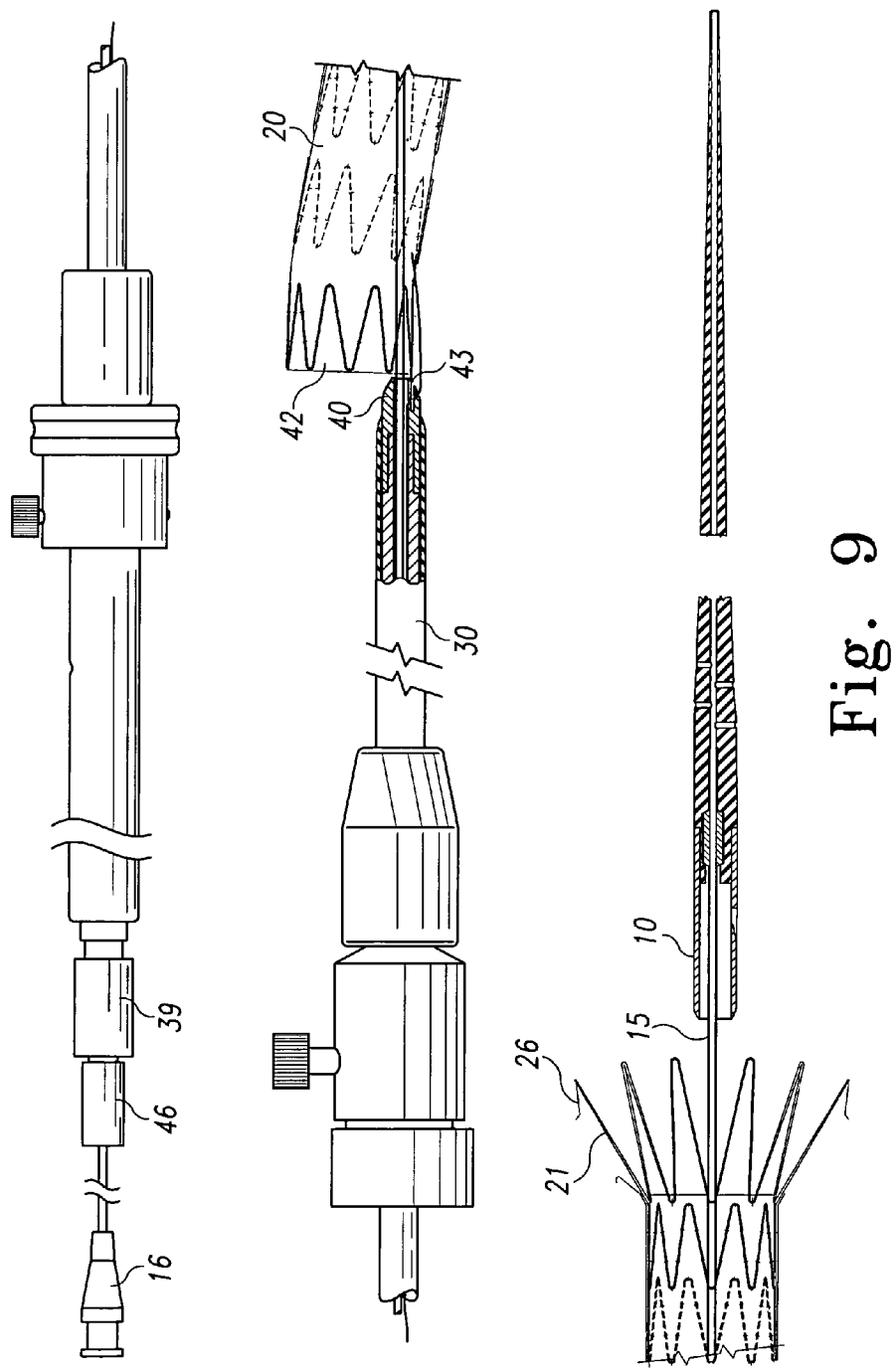
FIG. 9 is an exploded view partially in section of the introducer of FIG. 7 with the release of the proximal end stage of deployment.

In FIG. 9, the proximal trigger wire 22 has been removed, allowing the retention device 10 to be separated from the self-expanding zigzag stent 21, as explained above. At this stage, the proximal trigger wire release mechanism 24 and the proximal trigger wire 22 can be removed completely.

Also, the screw cap 46 of the pin vise 39 has been loosened so that the thin walled tubing 15 can been pushed in a proximal direction to move the proximal attachment means 10 in a proximal direction. When the proximal attachment means 10 no longer surrounds the self-expanding stent 21 at the proximal end of the prosthesis 20, the self-expanding stent 21 expands. When the self-expanding stent 21 expands, the hooks or barbs 26 on the self-expanding stent 21 grip into the walls of the lumen to hold the proximal end of the prosthesis 20 in place.

At this point, the distal end 42 of the prosthesis 20 is still retained by the distal attachment means 40, with the loop 43 retained therein. The external sheath 30 is then withdrawn to distal of the distal attachment section 40 to allow the distal end 42 of the prosthesis 20 to expand. At this point, the distal end 42 of the prosthesis 20 can still be moved. Consequently, the prosthesis 20 can still be rotated or lengthened or shortened or otherwise moved to for accurate positioning.

Figure 10:
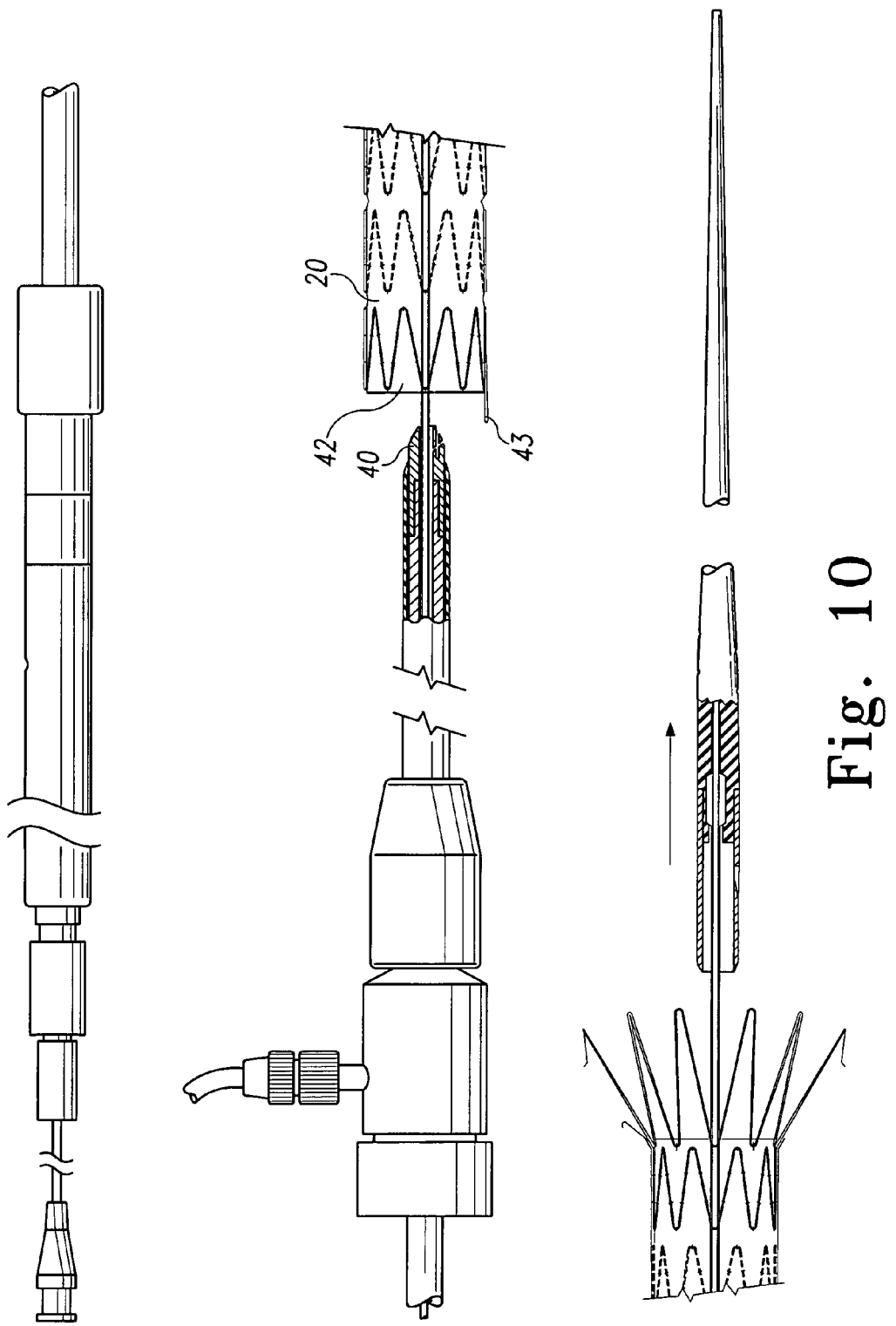
FIG. 10 is an exploded view partially in section of the introducer of FIG. 7 with the release of the distal end stage of deployment.

In FIG. 10, the distal end 42 of the prosthesis 20 has been released by removal of the distal trigger wire 44. At this stage, the distal trigger wire release mechanism 25 and the distal trigger wire 44 can be removed completely. This removal can be accomplished by passing the distal wire release mechanism 25 over the pin vise 39 and the connection means 16. The loop 43 of the terminal distal self-expanding zigzag stent 19 is hence released, and the prosthesis 20 is now free to expand to the wall of the lumen. At this point, the introducer is ready to be removed.

Figure 11:
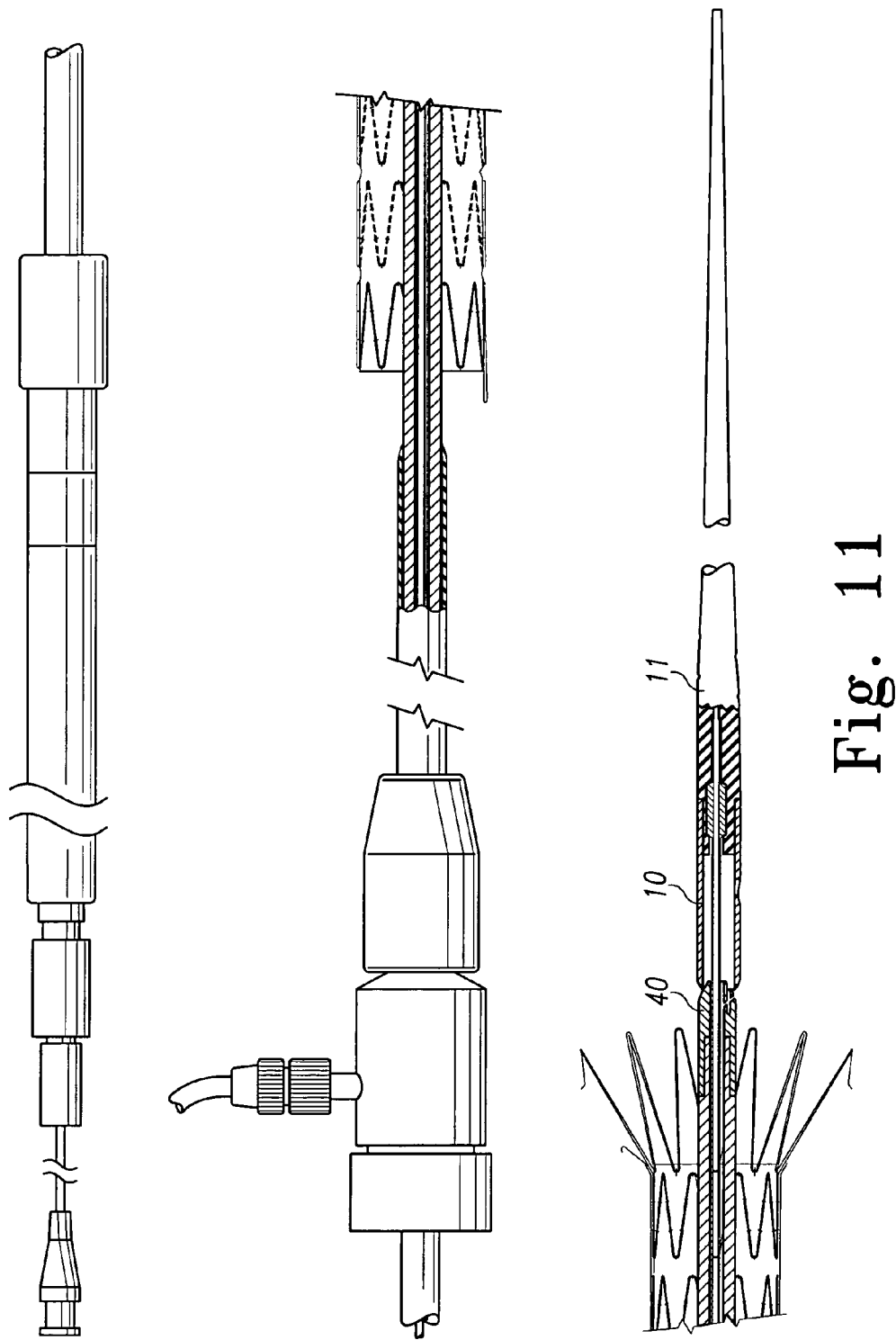
FIG. 11 is an exploded view partially in section similar to FIG. 10 showing the advancement of the distal attachment mechanism to the proximal attachment mechanism.

In FIG. 11, the first stage of removal is shown. First, the distal attachment section 40 is advanced until it is received in the rear of the proximal attachment device 10. Next, the proximal attachment device 10, the tapered flexible extension 11, and the distal attachment device 40 are removed together, as shown in FIG. 11.

Figure 12:
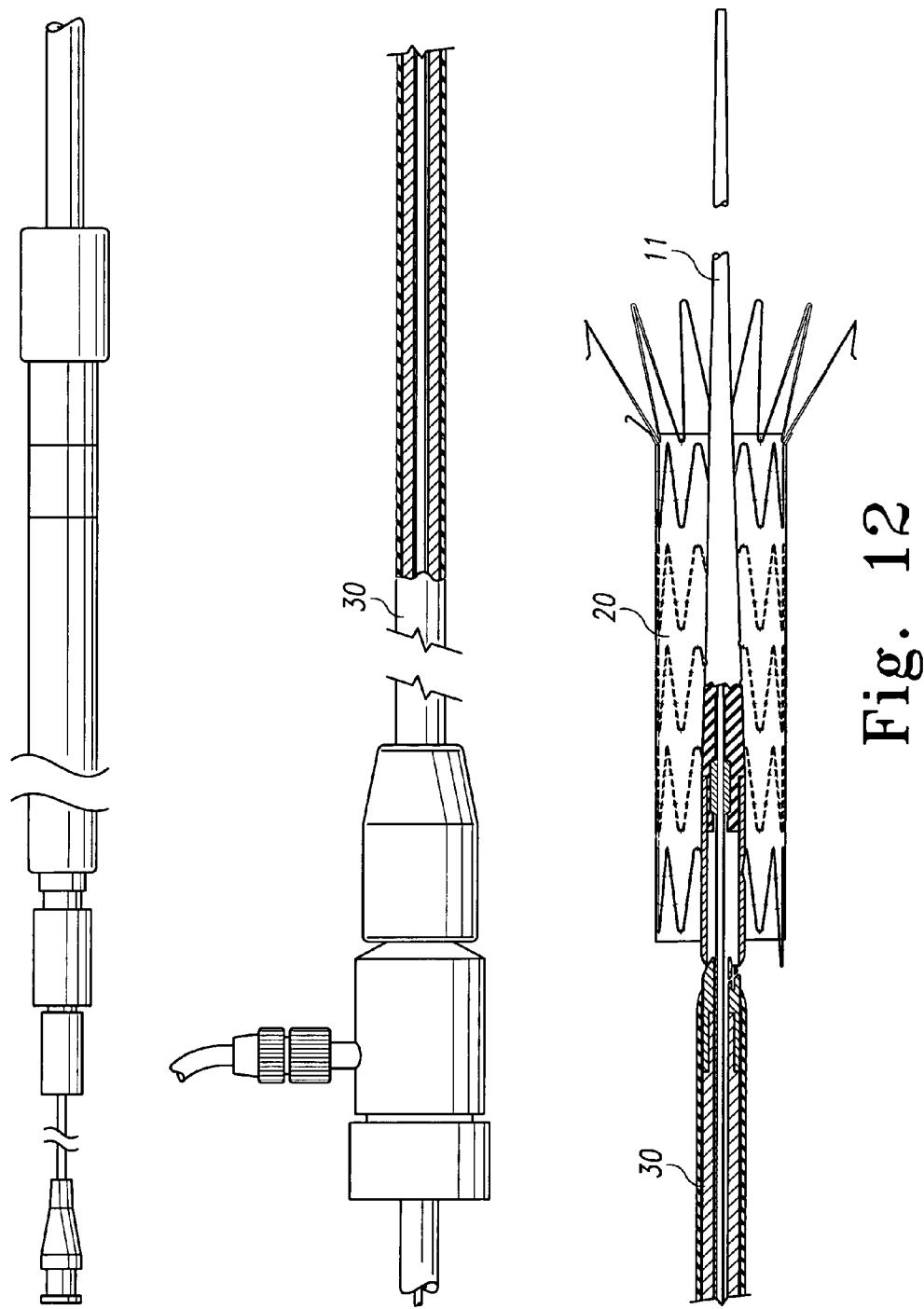
FIG. 12 is an exploded view partially in section similar to FIG. 10 showing the withdrawal of the introducer.

In FIG. 12, the sheath 30 has been advanced to uncover the joint between the proximal attachment device 10 and the distal attachment section 40. The sheath 30 can be removed with the proximal attachment device 10, the tapered flexible extension 11, and the distal attachment device 40. Alternatively, these items could be removed separately, followed by removal of the external sleeve 30.

Figure 13:
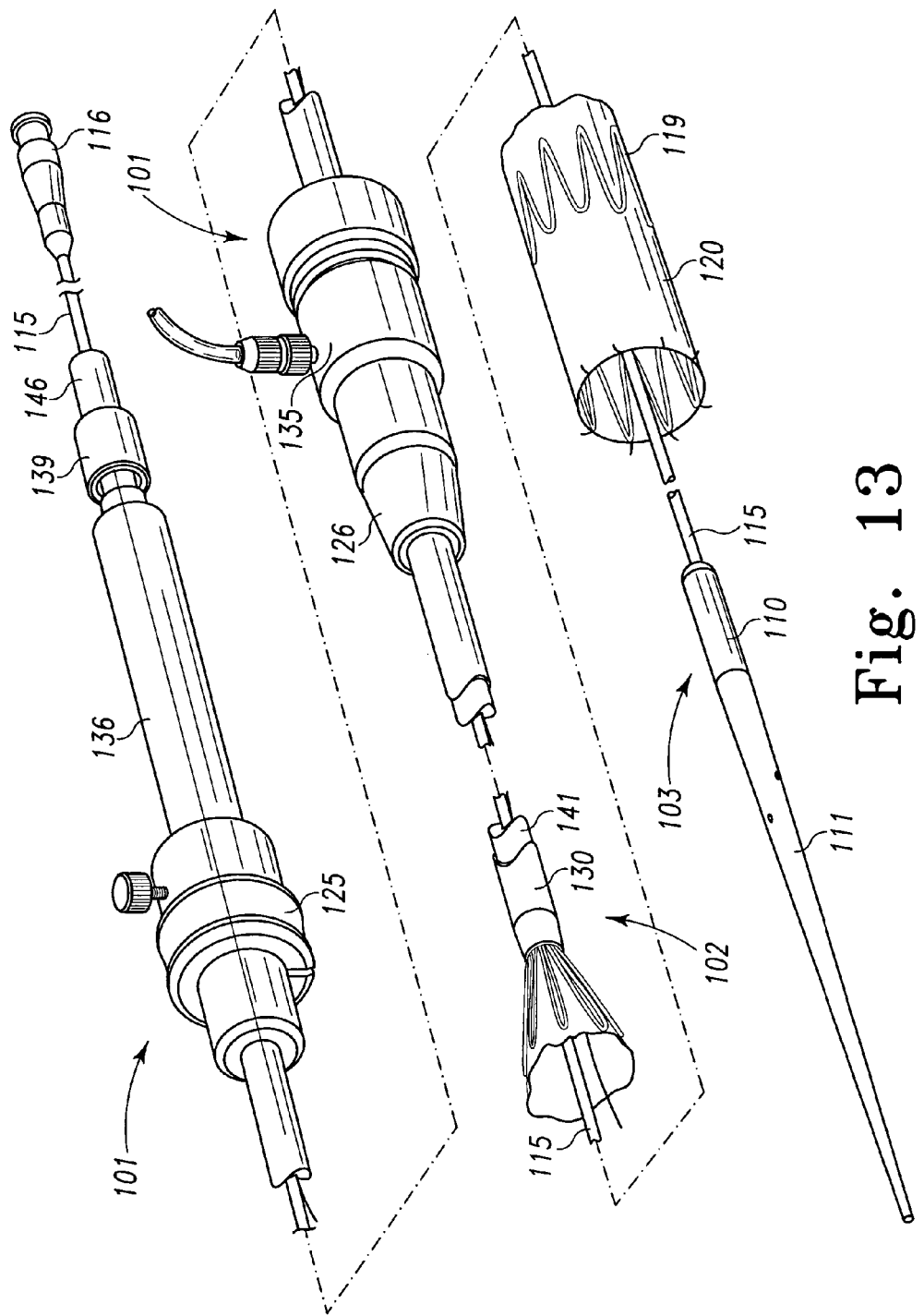
FIG. 13 is a perspective view of a second introducer with a branch prosthesis partially deployed.

FIG. 13 shows an endoluminal branch prosthesis 120, and an endovascular introducer for deploying the branch prosthesis 120. The branch prosthesis 120 is configured to have an outer diameter approximately equal to the diameter of the fenestration 17 of the prosthesis 20, so that the branch prosthesis 120 can be tightly coupled to the prosthesis 20.

The introducer includes an external manipulation section 101, a proximal positioning mechanism 102 and a distal positioning mechanism 103. The deployment of the prosthesis 120 and the actions of the distal and proximal attachment regions 103 and 102, and the manipulation section 101 are fundamentally the same as for the deployment of the prosthesis 20 described above.

As shown in FIGS. 14 and 15, one major difference between the branch prosthesis 120 and the prosthesis 20 is that the branch prosthesis 120 is loaded into the introducer "backwards", such that a self-expanding zigzag stent 121 is retained by the proximal positioning mechanism 102. Additionally, the "proximal" end of the branch prosthesis 120 is nearest to the external manipulation section 101, whereas the "proximal" end of the prosthesis 20 is farthest from the external manipulation section 1.

The branch prosthesis 120 comprises a tubular graft material 150, with self expanding stents 119 attached thereto. The tubular graft material 150 is preferably a non-porous material similar to the tubular graft material 50. The self expanding stents 119 cause the branch prosthesis 120 to expand following its disengagement from the introducer.

The branch prosthesis 120 also includes a self expanding zigzag stent 121 that extends from its proximal end. When it is disengaged, the self expanding zigzag stent 121 anchors the proximal end of the branch prosthesis 120 to the internal wall of the prosthesis 20.

FIGS. 14 and 15 illustrate proximal and distal retention and release mechanisms 102 and 103 of the introducer, respectively. During the placement phase of the medical procedure, the branch prosthesis 120 is retained in a compressed condition by a sheath 130.

During assembly of the introducer, the sheath 130 is advanced over a cylindrical sleeve 110 of the distal attachment region 103 while the branch prosthesis 120 is held in a compressed state by an external force. A proximal attachment retention section 140 is formed in a thick walled tube 141 to retain the proximal end of the branch prosthesis 120. Alternatively, the proximal attachment section 140 can be a separate piece coupled to the thick walled tube 141.

FIG. 14 shows the proximal attachment region 102 in greater detail. The tube 141 is coaxial with and radially outside a thin walled tube 115. The tube 141 is "thick walled". The sheath 130 is coaxial with and radially outside the thick walled tube 141. The thick walled tube 141 and the sheath 130 extend proximally and then distally to the manipulation region 101, as shown in FIG. 13.

The proximal end 142 of the prosthesis 120, including the self-expanding zigzag stent 121, is retained by the proximal attachment section 140 of the thick walled tube 141. The proximal end of the self-expanding zigzag stent 121 has a loop 143 through which a proximal trigger wire 144 extends. The proximal trigger wire 144 extends through an aperture 145 in the proximal attachment section 140 and into the annular region between the thin walled tube 115 and the thick walled tube 141.

FIG. 15 shows the distal attachment region 103 in greater detail. The distal attachment region 103 includes a cylindrical sleeve 110. The cylindrical sleeve 110 has a long tapered flexible extension 111 extending from its distal end. The flexible extension 111 has an internal longitudinal aperture 112. The thin walled tube 115 is fastened to the extension 111.

The distal most stent 119 is released by retracting the sheath 130, removing the trigger wire 122, and then sliding the distal attachment region 103, including the retention device 110, distally away from the distal most stent 119. Once the retention device 110 has cleared the distal most stent 119, the distal most stent 119 will expand. The distal most stent 119 can include barbs, as shown in FIG. 16, to facilitate anchoring the stent 119 to the lumen.

The trigger wire 122 and the distal wire release mechanism 124 form a control member to selectively release the retention device 110 from the prosthesis 120 by holding the distal most stent 119 in the retention device 110 until the prosthesis 120 is positioned at a desired site in the lumen.

Figure 16:
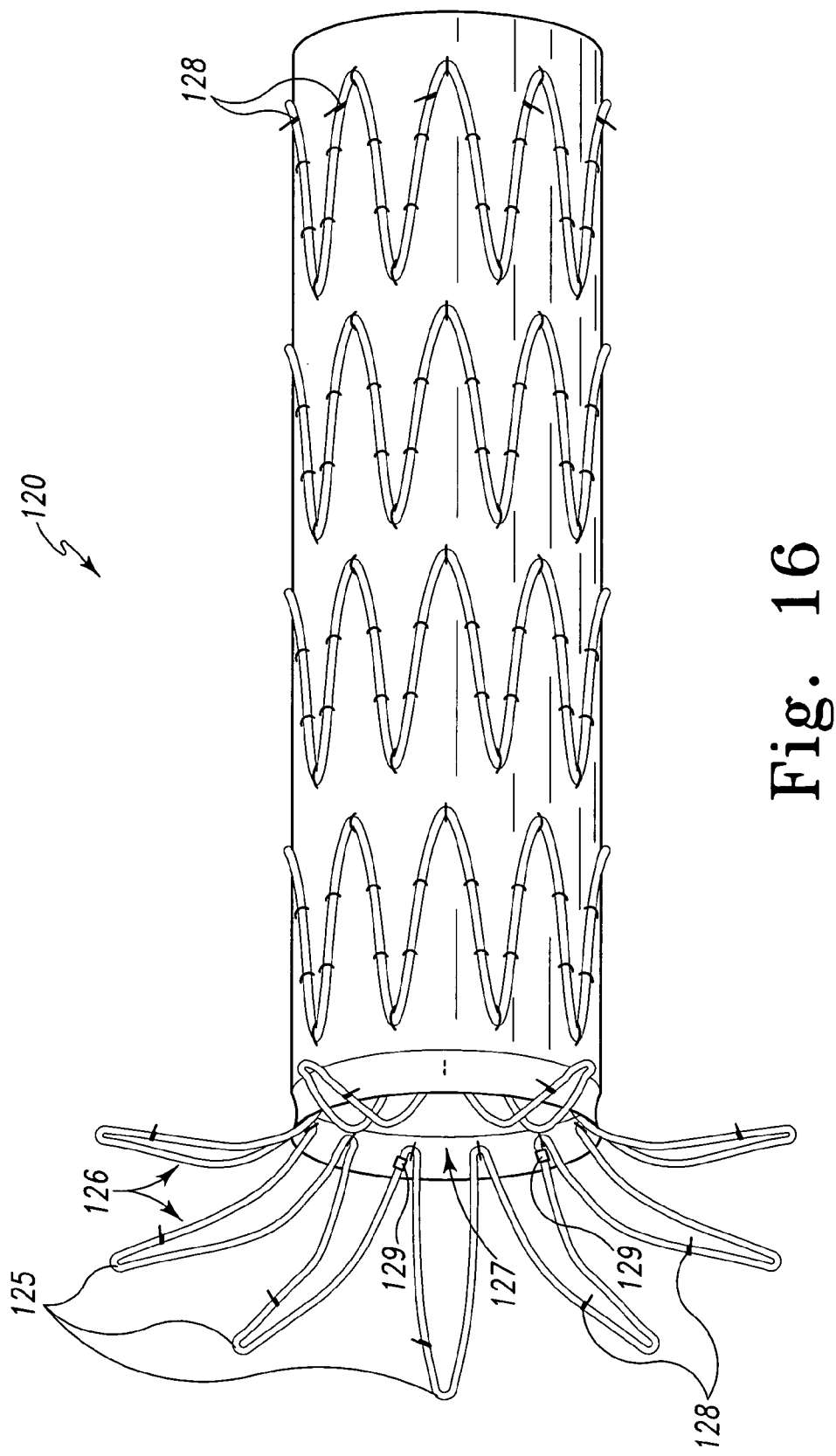
FIG. 16 is an isometric view of the branch prosthesis shown in FIG. 13.

FIG. 16 is an isometric view of the branch prosthesis 120. As shown in FIG. 16, when fully expanded the self-expanding zigzag stent 121 has a curvature to facilitate anchoring of the branch prosthesis 120 to an interior wall of the prosthesis 20. Outer portions of the self expanding stent 121 are seen to extend substantially radially outwardly from the tubular graft 150. The self-expanding zigzag stent 121 allows the branch prosthesis 120 to resist the force of blood flow, which may tend to dislodge the branch prosthesis 120 from the prosthesis 20.

The self-expanding zigzag stent 121 can have a parabolic or round curvature so that an end 125 of a loop 126 is located in about the same plane as an opening 127 of the branch prosthesis 120. The self-expanding zigzag stent 121 can be mounted near the opening 127 of the branch prosthesis 120, so the curvature of one loop 126 of the stent 121 is between about 120° and 200°, and preferable between about 170° and 190°.

The distal most stent 119 can have barbs 128 attached thereto. The barbs 128 can anchor the stent 119 to the lumen so that the branch prosthesis 120 does not slide into the prosthesis 20. As mentioned above, hydrostatic forces in arteries, where blood flows from main vessels to branch vessels, will be significantly greater in the proximal to distal direction than in the reverse direction. Therefore, the self-expanding zigzag stent 121 will resist the greater force, and the barbs 128 coupled to the stent 119 will resist the lesser force, so that the branch prosthesis 120 remains securely anchored within the fenestration 17 of the main prosthesis 20.

Radiographic markers 129 can be attached to the self-expanding zigzag stent 121, to one of the stents 119 or to the tubular graft material 150. For example, the radiographic markers 129 can be small rings of metal, such as stainless steel, wrapped around the stent 121 or one of the stents 119, or sewn to the tubular graft material 150 with suture. Preferably, at least one radiographic marker 129 is located near the opening 127, so that the opening 127 can be aligned with the fenestration 17 of the graft 20.

FIG. 17 is a front view of a main lumen 175 and a branch lumen 176, wherein the lumens 175 and 176 are in fluid communication with each other. The main lumen 175 has an aneurism, or weakness, which exists at the attachment point of the branch lumen 176. FIG. 18 shows the lumens 175 and 176 after the prosthesis 20 has been successfully implanted. The fenestration 17 is aligned with the opening of the branch lumen 176.

FIG. 19 shows the lumens 175 and 176 after the prosthesis 120 has been successfully implanted. The prosthesis 20 reinforces the main lumen 175. The branch prosthesis 120 performs two main functions. First, the branch prosthesis 120 keeps the fenestration 17 aligned so that the lumens 175 and 176 remain in fluid communication. Second, the branch prosthesis 120 reinforces the branch lumen 176, which may also be weakened because of the aneurism.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but can reside in two or more of these combined together. Accordingly, the invention is not to be restricted except in light of the attached claims and their equivalents.

The invention claimed is:

1. An intraluminal prosthesis for strengthening a main lumen and a branch lumen in direct fluid communication with the main lumen, the prosthesis comprising:
    a first graft comprising a first tubular flexible body including a wall with an interior and a fenestration through the wall;
    a second graft having a second tubular flexible body and a proximal end and a distal end, wherein the fenestration of the first graft is dimensioned to receive the second tubular flexible body; and
    a self-expanding zigzag stent configured to anchor said second graft to the first graft, the self-expanding zigzag stent including a plurality of connecting segments and bends interconnecting the connecting segments, the bends comprising a set of proximal bends and a set of distal bends, the distal bends of the self-expanding zigzag stent attached to the proximal end of the second graft, wherein each of the connecting segments of the self-expanding zigzag stent includes a concave curvature configured to extend each connecting segment proximally away and radially outward from the proximal end of the second graft, wherein the self-expanding zigzag stent extends through the fenestration, and the proximal bends are disposed substantially radially outward from the fenestration and contact the first graft interior wall.

2. The intraluminal prosthesis of claim 1, wherein the self-expanding zigzag stent is a proximal self-expanding zigzag stent, the prosthesis further comprising a distal self-expanding zigzag stent including a plurality of connecting segments and bends interconnecting the connecting segments, the bends comprising a set of proximal bends attached along the distal end of the second graft, and a set of distal bends having attachment barbs configured to anchor into said branch lumen.

3. The intraluminal prosthesis of claim 1 wherein the first graft further comprises a plurality of self-expanding stents that are coupled along the length of the first tubular flexible body.

4. The intraluminal prosthesis of claim 1 wherein the self-expanding zigzag stent is a proximal self-expanding zigzag stent, and wherein the second graft further comprises a plurality of self-expanding stents that are coupled along the length of the second tubular flexible body distal the proximal zigzag self-expanding stent.

5. The intraluminal prosthesis of claim 1 wherein the first graft is configured to be positioned inside a main lumen, and the second graft is configured to be positioned substantially inside a branch lumen connected to the main lumen.

6. The intraluminal prosthesis of claim 1 wherein the first graft further comprises a terminal self-expanding stent mounted to a proximal end of the first tubular flexible body, the terminal stent extending beyond said proximal end of the first tubular flexible body.

7. The intraluminal prosthesis of claim 6 wherein the terminal stent includes attachment barbs.

8. The intraluminal prosthesis of claim 1 wherein the second tubular flexible body comprises a graft material, and the self-expanding stent is not covered by the graft material of the second tubular flexible body.

9. The intraluminal prosthesis of claim 8 wherein the proximal bends of the self-expanding stent of the second graft include attachment barbs configured to anchor into the first graft interior wall.

10. An intraluminal prosthesis for strengthening a branch lumen configured to couple to an interior wall of a second intraluminal prosthesis through a fenestration, the prosthesis comprising:
    a tubular flexible body about a branch axis having a proximal end and a distal end; and
    a self-expanding zigzag stent including a plurality of connecting segments and bends interconnecting the connecting segments, the bends comprising a set of proximal bends having attachment barbs, and a set of distal bends attached to the proximal end of the body, wherein each of the connecting segments includes a concave curvature configured to extend each connecting segment proximally away and radially outward from the proximal end of the prosthesis body, wherein the self-expanding zigzag stent is configured to extend through said fenestration of the second prosthesis, and the attachment barbs of the proximal bends are disposed substantially radially outward from the prosthesis body to anchor into the interior wall of said second prosthesis.

11. The intraluminal prosthesis of claim 10, wherein the self-expanding zigzag stent is a proximal self-expanding stent, the prosthesis further comprising a distal self-expanding stent including a plurality of connecting segments and bends interconnecting the connecting segments, the bends comprising a set of proximal bends attached along the distal end of the prosthesis body, and a set of distal bends having attachment barbs configured to anchor into said branch lumen.

12. The intraluminal prosthesis of claim 10, wherein a plane is defined by the proximal end of the prosthesis body and perpendicular to said branch axis, and said proximal bends are disposed at an angle between about 120° and about 200° relative to said plane.

13. The intraluminal prosthesis of claim 10, wherein the flexible body is a body portion of a renal prosthetic device.

14. The intraluminal prosthesis of claim 10, wherein the flexible body is a body portion of a superior mesenteric prosthetic device.

15. The intraluminal prosthesis of claim 10, wherein the flexible body is a body portion of a celiac prosthetic module.

16. The intraluminal prosthesis of claim 10, wherein the flexible body is a body portion of a left common carotid prosthetic device.

17. The intraluminal prosthesis of claim 10, wherein the flexible body is a body portion of a left subclavian prosthetic device.

18. The intraluminal prosthesis of claim 10, wherein the flexible body is a body portion of an innominate prosthetic device.

19. The intraluminal prosthesis of claim 10, wherein the flexible body is a body portion of a hypogastric prosthetic device.

20. An intraluminal prosthesis for strengthening a main lumen and a branch lumen in direct fluid communication with the main lumen, the prosthesis comprising:
    a first graft comprising a tubular body including a wall with an interior and a fenestration through the wall;
    a second graft having a tubular body about a branch axis and a proximal end and a distal end, wherein the fenestration of the first graft is dimensioned to receive the second graft body; and a self-expanding zigzag stent configured to anchor said second graft to the first graft, the self-expanding zigzag stent including a plurality of connecting segments and bends interconnecting the connecting segments, the bends comprising a set of proximal bends including attachment barbs and a set of distal bends attached to the proximal end of the second graft, wherein each of the connecting segments of the self-expanding zigzag stent includes a concave curvature configured to extend each connecting segment proximally away and radially outward from a plane defined by the proximal end of the second graft, the plane perpendicular to said branch axis, so that each of the proximal bends are located approximately in said plane, wherein the self-expanding zigzag stent extends through the fenestration, and the proximal bends are disposed substantially radially outward from the fenestration and the attachment barbs of the proximal bends anchor into the first graft interior wall.

21. An intraluminal prosthesis for strengthening a main lumen and a branch lumen in direct fluid communication with the main lumen, the prosthesis comprising:

a first graft comprising a tubular body including a wall with an interior and a fenestration through the wall;

a second graft having a tubular body, a proximal end, and a proximal opening at the proximal end, where the proximal opening lies in a plane perpendicular to a longitudinal axis of the second graft; and a self-expanding stent disposed at a proximal end of the second graft and configured to anchor a portion of the second graft to and within the first graft, and including a plurality of interconnected loops having first and second ends, each loop attached at the first end to the proximal opening of the second graft, and the second end extending radially away from the proximal opening of the second graft, where each loop has a curvature of between about 120 degrees and 200 degrees from the plane defined by the proximal opening, where the proximal end of the second graft is positioned at the fenestration of the first graft so that the proximal end of the stent is disposed substantially radially outward from the fenestration to anchor into the interior wall of the first graft.

22. The intraluminal prosthesis of claim 21, wherein at least one of the second ends of the interconnected loops includes an attachment barb.

23. The intraluminal prosthesis of claim 22, wherein the curvature of each loop is between about 170 degrees and 190 degrees.

24. The intraluminal prosthesis of claim 23, wherein the second end is located in about the same plane as the proximal opening.

25. The intraluminal prosthesis of claim 21, wherein the curvature of each loop is a parabolic curvature.

* * * * *